US012622892B2

(12) United States Patent
Safe et al.

(10) Patent No.: US 12,622,892 B2
(45) Date of Patent: May 12, 2026

(54) METHODS FOR TREATING ENDOMETRIOSIS

(71) Applicant: THE TEXAS A&M UNIVERSITY SYSTEM, College Station, TX (US)

(72) Inventors: Stephen Safe, Tamu College Station, TX (US); Kumaravel Mohankumar, Tamu College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 762 days.

(21) Appl. No.: 17/904,814

(22) PCT Filed: Feb. 24, 2021

(86) PCT No.: PCT/US2021/019402
§ 371 (c)(1),
(2) Date: Aug. 23, 2022

(87) PCT Pub. No.: WO2021/173660
PCT Pub. Date: Sep. 2, 2021

(65) Prior Publication Data
US 2023/0113363 A1 Apr. 13, 2023

Related U.S. Application Data
(60) Provisional application No. 62/981,431, filed on Feb. 25, 2020.

(51) Int. Cl.
*A61K 31/40* (2006.01)
*A61K 31/404* (2006.01)
*A61P 15/00* (2006.01)

(52) U.S. Cl.
CPC ............ *A61K 31/404* (2013.01); *A61P 15/00* (2018.01)

(58) Field of Classification Search
CPC ............................ A61K 31/404; C07D 403/06
See application file for complete search history.

(56) References Cited

U.S. PATENT DOCUMENTS

| | | | |
|---|---|---|---|
| 8,389,563 | B2 | 3/2013 | Safe |
| 8,580,843 | B2 | 11/2013 | Tjalkens et al. |
| 2001/0047029 | A1 | 11/2001 | Handelsman |
| 2002/0147155 | A1 | 10/2002 | Foster et al. |
| 2003/0130335 | A1 | 7/2003 | Mjalli |
| 2006/0084694 | A1 | 4/2006 | Safe |
| 2010/0087504 | A1 | 4/2010 | Tjalkens |
| 2016/0037773 | A1 | 2/2016 | Qian et al. |
| 2016/0303081 | A1 | 10/2016 | Safe |
| 2017/0009272 | A1 | 1/2017 | Yousuf |
| 2018/0312568 | A1 | 11/2018 | Hedrick et al. |
| 2018/0320170 | A1 | 11/2018 | Konieczka et al. |
| 2020/0239448 | A1 | 7/2020 | Safe et al. |
| 2021/0401823 | A1 | 12/2021 | Sacher et al. |
| 2022/0265606 | A1 | 8/2022 | Safe et al. |
| 2023/0113363 | A1 | 4/2023 | Safe et al. |

FOREIGN PATENT DOCUMENTS

| | | | |
|---|---|---|---|
| CA | 3072456 | A1 | 2/2019 |
| CN | 1268134 | | 9/2000 |
| CN | 1268134 | A | 9/2000 |
| CN | 103342675 | A | 10/2013 |
| CN | 10545237 | | 4/2016 |
| CN | 110573146 | A | 12/2019 |
| EP | 0887348 | | 12/1998 |
| JP | 2002507206 | | 3/2002 |
| WO | 99/00381 | A1 | 1/1999 |
| WO | 9900381 | | 1/1999 |
| WO | 02/36561 | A1 | 5/2002 |
| WO | 2006023891 | | 3/2006 |
| WO | 2006133943 | | 12/2006 |
| WO | 2012065139 | | 5/2012 |
| WO | 2014002613 | A1 | 2/2014 |
| WO | 2017/161374 | A1 | 9/2017 |
| WO | 2019/032902 | A1 | 2/2019 |
| WO | 2019/183527 | A1 | 9/2019 |
| WO | 2021/022220 | A2 | 2/2021 |
| WO | 02/080906 | A1 | 10/2022 |

OTHER PUBLICATIONS

No new reference.*
Canadian Office Action mailed on Feb. 19, 2024, issued in Canadian Application No. 3,173,724, filed on Feb. 24, 2021; 3 pages.
Chinese Decision on Rejection mailed on Jun. 17, 2024, issued in Chinese Application No. 202080068950.1, filed on Jul. 31, 2020; 10 pages.
Japanese Notice of Reasons for Rejection mailed on Jul. 30, 2024, issued in Japanese Application No. 2022-506375, filed on Jul. 31, 2020; 11 pages.
Decision of Rejection mailed on Mar. 20, 2023, issued in Japanese Application No. 2023-118472, filed on Aug. 9, 2018; 6 pages.
Canadian Office Action mailed on Feb. 19, 2024, issued in Canadian Application No. 3,072,456, filed on Aug. 9, 2018; 6 pages.
European Supplementary Search Report mailed on Apr. 2, 2024, issued in European Application No. 21760941.1, filed on Feb. 24, 2021; 12 pages.
Liu, et al., "Overexpression of TGF-B enhances the migration and invasive ability of ectopic endometrial cells via ERK/MAPK signaling pathway," Experimental and Therapeutic Medicine 17: 4457-4464, 2019.
Palumbo-Zerr, K. et al., "Orphan nuclear receptor NR4A1 regulates transforming growth factor-B signaling and fibrosis," Nature Medicine, vol. 21, No. 2, Feb. 2015, pp. 150-160.

(Continued)

*Primary Examiner* — Shawquia Jackson
(74) *Attorney, Agent, or Firm* — CHRISTENSEN O'CONNOR JOHNSON KINDNESS PLLC

(57) ABSTRACT

Methods of treating endometriosis through modulation of Nuclear Receptor Subfamily 4 Group A Member 1 (NR4A1) activity including administration of an NR4A1 ligand to an individual in need thereof are described. In an embodiment, the compounds include methylene substituted diindolylmethanes.

26 Claims, 31 Drawing Sheets

(56) References Cited

OTHER PUBLICATIONS

Safe, S. et al., "Orphan nuclear receptor 4A1 (NR4A1) and novel ligands," Essays in Biochemistry (2021) 65; 877-886. <https://doi.Org/10.1042/EBC20200164>.

Non-Final Office Action mailed on Jul. 30, 2024 in U.S. Appl. No. 17/510,904, filed Oct. 26, 2021; 24 pages.

Safe, S. et al., "Nuclear Receptor 4A (NR4A) Family—Orphans No More," J Steroid Biochem Mol Biol. Mar. 2016; 157: 48-60. doi:10.1016/j.jsbmb.2015.04.016.

Huang, Z. et al., "3,3' -Diindolylmethane decreases VCAM-1 expression and alleviates experimental colitis via a BRCA1-dependent antioxidant pathway," Elsevier: Free Radical Biology & Medicine 50 (2011) 228-236.

Australian Examination Report mailed on Mar. 26, 2025, issued in Australian Application No. 2020320289; 5 pages.

Australian Examination Report mailed on Nov. 30, 2023, issued in Australian Application No. 2023203349, filed on Jul. 31, 2020, 3 pages.

Extended European Search Report mailed on Jul. 21, 2023, issued in European Application No. 20846800.9, filed on Jul. 31, 2020, 11 pages.

First Chinese Office Action mailed on Sep. 5, 2023, issued in Chinese Application No. 202180030854.0, filed on Aug. 23, 2022, 13 pages.

Second Chinese Office Action mailed om Dec. 29, 2023, issued in Chinese Application No. 202080068950.1, filed on Jul. 31, 2020, 8 pages.

Lee, S.O. et al., "Diindolylmethane Analogs Bind NR4A 1 and Are NR4A 1 Antagonists in Colon Cancer Cells," Mol Endocrinol. Oct. 2014, 28(10):1729-1739.

Mattiazzi, J. et al. "Incorporation of 3,3'-Diindolylmethane into Nanocapsules Improves Its Photostability, Radical Scavenging Capacity, and Cytotoxicity Against Glioma Cells," AAPS PharmSciTech, (2019) 20:49, pp. 1-11.

Mohankumar, K. et al., "Nuclear Receptor 4A1 (NR4A1) Antagonists Induce ROSdependent Inhibition of mTOR Signaling in Endometrial Cancer," Gynecol Oneal. Jul. 2019; I 54(1): 218-227. doi: 10.1016/j.ygyno.20?9 04.678.

Morales-Prieto, D. M. et al., "Comparison of dienogest effects upon ,'-diindolylmethane supplementation in models of endometriosis and clinical cases," Science Direct: Reproductive Biology, vol. 18, Issue 3, Sep. 2018, pp. 252-258.

Rahimi, M. et al., "3,3'-Diindolylmethane (DIM) inhibits the growth and invasion of drug-resistant human cancer cells expressing EGFR mutants," Elsevier: Cancer Letters 295 (2010) 59-68.

International Search Report mailed Nov. 26, 2018, for International Application No. PCT/US2018/046115. (5 pages).

Written Opinion mailed Nov. 26, 2018, for International Application No. PCT/US2018/046115. (5 pages).

Chakrabarty et al., Document No. 145:438485, retrieved from CAPLUS, 2006.

Zhang et al., Document No. 143:347015, retrieved from CAPLUS, 2005.

Palaniappan et al., Document No. 143:327199, retrieved from CAPLUS, 2005.

Rani et al., Document No. 156:533580, retrieved from CAPLUS, 2012.

Ghorbani-Vaghei et al., Document No. 153:358813, retrieved from CAPLUS, 2010.

Lala, P.K. and Orucevic, A., "Role of nitric oxide in tumor progression: Lessons from experimental tumors," Cancer and Metastasis Reviews, 17(1):91-106, 1998.

Golub, T.R. et al., "Molecular Classification of Cancer: Class Discovery and Class Prediction by Gene Expression Monitoring," Science, 286:531-537, Oct. 15, 1999.

"Cancer" [online: MedlinePlus], retrieved from the Internet <http://www.nlm.nih.gov/medlineplus/cancer.html> [retrieved on Jul. 6, 2007], 10 pages.

Notice of Deficiencies dated Mar. 16, 2022 in corresponding Israeli Patent Application No. 272571, 6 pages.

Das Pranab J et al, "Synthesis of aryl/alkyl(2,2'-bis-3-methylindolyl)methanes and aryl(3,3'-bis indolyl)methanes promoted by secondary amine based ionic liquids and microwave irradiation", Tetrahedron Letters, Jun. 28, 2012, vol. 53, No. 35, doi:10.1016/J.TETLET.2012.06.106, ISSN 0040-4039, pp. 4718-4720.

Scientific Exchange Inc., Registry, Chemical Abstracts Service, Columbus, Ohio, US, (Jul. 16, 2006), Database accession No. 893250-47-0.

ChemBridge Corp, Registry, Chemical Abstracts Service, Columbus, Ohio, US, (Jun. 17, 2004), Database accession No. 694442-88-1.

Kamal Ahmed et al, "Synthesis, anticancer activity and apoptosis inducing ability of bisindole linked pyrrolo[2,1-c] [1,4]benzodiazepine conjugates", Biorganic & Medicinal Chemistry Letters, Elsevier, Amsterdam , NL, Oct. 31, 2011, vol. 22, No. 1, doi:10.1016/J.BMCL.2011.10.080, ISSN 0960-894X, pp. 571-578.

Joshi R S et al, "Ultrasound assisted green synthesis of bis(indol-3-yl)methanes catalyzed by 1-hexenesulphonic acid sodium salt", Ultrasonics: Sonochemistry, Butterworth-Heinemann, GB, vol. 17, No. 2, doi:10.1016/J.ULTSONCH.2009.08.015, ISSN 1350-4177, Aug. 29, 2009, pp. 298-300.

Registry, Chemical Abstracts Service, Columbus, Ohio, US, (Jun. 17, 2004), Database accession No. 694444-38-7.

Naidu, Kalla Reddi Mohan; Khalivulla, Shaik Ibrahim; Rasheed, Syed; Fakurazi, Sharida; Arulselvan, Palanisamy; asekan, Ola; Abas, Faridah, Synthesis of bisindolylmethanes and their cytotoxicity properties, International Journal of Molecular Science, 2013, 14, 1843-1853.

Sharma, Deepak K.; Rah, Bilal; Lambu, Mallikharjuna R.; Hussain, Altaf; Yousuf, Syed K.; Tripathi, Anil K.; Singh, Baldev; Jamwal, Gayatri; Ahmed, Zabeer; Chanauria, Nayan; Nargotra, Amit; Goswami, Anindya; Mukherjee, Debaraj, Design and synthesis of novel N, N'-glycoside derivatives of 3, 3'-diindolylmethanes as potential antiproliferative agents, MedChem Comm, 2012, 3(9), 1082-1091.

Velasco-Bejarano, Benjamin; Sanchez-Torres, Luvia Enid; Garcia-Estrada, Jose Guadalupe; Miranda-Ruvalcaba, Rene; Alvarez-Toledano, Cecilio; Penieres-Carrillo, Guillermo, Diindolylmethane derivatives as apoptosis inductors in L5178y cells, Journal of the Mexican Chemical Societ., 2008, 52(3), 224-228.

Nasreen, Aayesha; Varala, Ravi; Rao, Kulakarni Sripad, A green protocol for the synthesis of bis(indolyl)methanes catalyzed by succinic acid under microwave irradiation, Organic Communications, 2017, 10(2), 104-113.

Database Registry, 2006, RN 893250-92-5, 893250-47-0, 892218-53-0, 694453-96-8, 694444-38-7, 694442-88-1, Retrieved from STN international [online]; retrieved on Aug. 2, 2022.

Zhan, Yan-yan, et al., The orphan nuclear receptor Nur77 regulates LKB1 localization and activate AMPK, Nature Chemical Biology, 2012, 8, 897-904.

English Translation of Japanese Notice of Reasons for Rejection mailed on Aug. 22, 2022, issued in corresponding Japanese Application No. 2020-507693, filed on Aug. 9, 2018, 7 pages.

Examination Report mailed Nov. 8, 2022, issued in corresponding Australian Application No. 2018313925, filed Aug. 9, 2018, 10 pages.

Rani, V. Jhansi, K. Veena Vani, and C. Venkata Rao. "PEG-SO3H as a Catalyst for the Preparation of Bis-Indolyl and Tris-Indolyl Methanes in Aqueous Media." Synthetic Communications 42.14 (2012): 2048-2057. CAS RN 692290-53-2, Retrieved from STNext [online] on May 22, 2021.

Challa, Chandrasekhar, et al. "Expedient synthesis of indolo [2, 3-b] quinolines, chromeno [2, 3-b] indoles, and 3-alkenyl-oxindoles from 3, 3'-diindolylmethanes and evaluation of their antibiotic activity against methicillin-resistant *Staphylococcus aureus*." ACS omega 2.8 (2017): 5187-5195.

Islam, Md Ataul, and Tahir S. Pillay. "Structural requirements for potential HIV-integrase inhibitors identified using pharmacophore-based virtual screening and molecular dynamics studies." Molecular Biosystems 12.3 (2016): 982-993.

(56) References Cited

OTHER PUBLICATIONS

Sarva, Santhisudha, et al. "Synthesis, antibacterial and anti-inflammatory activity of bis (indolyl) methanes." Chinese Chemical Letters (2015).
Khan, Khalid Mohammed, et al. "Evaluation of bisindole as potent β-glucuronidase inhibitors: Synthesis and in silico based studies." Bioorganic & medicinal chemistry letters 24.7 (2014): 1825-1829.
Substances/CAS RNs 315235-11-1 (Jan. 19, 2001), 486994-88-1 (Feb. 7, 2003), 486442-81-3 (Feb. 6, 2003), 510765-97-6 (May 5, 2003), 898679-19-1 (Aug. 4, 2006), 893251-07-5 (Jul. 16, 2006), and 486994-82-5 (Feb. 7, 2003), Retrieved from SciFinder [online) on Dec. 6, 2022.
Substances/CAS RNs 496839-88-4 (Mar. 4, 2003), 666818-76-4 (Mar. 24, 2004), 666818-70-8 (Mar. 24, 2004), 694453-96-8 (Jun. 17, 2004), 737769-31-2 (Sep. 2, 2004), 666818-67-3 (Mar. 24, 2004), 892225-57-9 (Jul. 12, 2006), and 693832-30-3 (Jun. 16, 2004), Retrieved from SciFinder [online) on Dec. 6, 2022.
Substances/CAS RNs 693827-98-4 (Jun. 16, 2004), 694447-96-6 (Jun. 17, 2004), 694447-49-9 (Jun. 17, 2004), and 893250-85-6 (Jul. 16, 2006), Retrieved from SciFinder [online) on Dec. 6, 2022.
First Chinese Office Action mailed on Sep. 26, 2022, issued in corresponding Chinese Application No. 2018800657931, filed Aug. 9, 2018, and its English translation thereof, 13 pages.
Rekha, et al. (abstract) Journal of Industrial and Engineering Chemistry (Amsterdam, Netherlands) (2013), 19 (1), 337-346. Acession No. 2012:1769704 retrieved from CAPLUS.
Mohankumar, Kumaravel et al., "Nuclear Receptor 4A1 (NR4A1) Antagonists Induce ROS-depende3nt Inhibition of mTOR Signaling in Endometrial Cancer," Gynecologic Oncology, vol. 154(1): 2019, 19 pages.
Lee, Syng-Ook et al., "Diindolylmethane Analogs Bind NR4A1 and Are NR4A1 Antagonists in Colon Cancer Cells," Molecular Endocrinology, vol. 28(10): Oct. 2014, pp. 1729-1739.
Mohankumar, Kumaravel et al., "Bis-Indole-Derived NR4A1 Ligands and Metformin Exhibit NR4A1-Dependent Glucose Metabolism and Uptake in C2C12 Cells," Endocrinology, vol. 159-(5), May 2018, 24 pages.
Lee, Syng-Ook et al., "Targeting NR4A1 (TR3) in Cancer Cells and Tumors," Expert Opinion on Therapeutic Targets, vol. 15(2): Feb. 2011, 20 pages.
Mohan, R. et al., "Synthesis of Bid(indolyl)methanes Using Hyper-Cross-Linked Polyaromatic Spheres Decorated with Bromemethyl Group as Efficient and Recyclable Catalysts," ACS Omega 2018, 3, 2242-2253.
Gopalalah, K. et al., "Iron-Catalyzed Oxidative Coupling of Benzylamines and Indoles: Novel Approach for Synthesis of Bis(indolyl)methanes," Synthesis 2015, 47, 1766-1774.
Palaniappan, S. and A. John, "Facile synthesis of bis(indolyl)methanes using polyindole salt as reusable catalyst," Elsevier: Journal of Molecular Catalysis A: Chemical 242 (2005) 168-172.
Bharate, S. B. et al., "Discovery of 3,3'-diindolylmethanes as potent antileishmanial agents," Elsevier: European Journal of Medicinal Chemistry 63 (2013) 435-443.
Japanese Office Action mailed on Mar. 17, 2025, issued in Japanese Application No. 2022-506375; 6 pages.
Jejurkar, V. P. et al., "Environmentally Benign, Highly Efficient and Expeditious Solvent-Free Synthesis of Trisubstituted , , Methanes Catalyzed y Sulfated Polyborate," ChemistrySelect 2017, 2, 11693-11696.
Olyaei, A. et al., "A novel approach to bis(indolyl)methanes using nickel nanoparticles as reusable catalyst under solvent-free conditions," J. Serb. Chem. Soc. 78 (4) 463-468 (2013).
Modak, A. et al., "Highly Porous Organic Polymer containing Free-CO2H Groups: A Convenient Carbocatalyst for Indole C-H Activation at Room Temperature," ChemCatChem 2013, 5, 1749-1753.
Zhang, Y. et al., "Room-Temperature Synthesis of Diindolylmethanes Using Silica-Supported Sulfuric Acid as a Reusable Catalyst Under Solvent-Free Conditions," Synthetic Communications, 41:16, 2446-2454.
Second Chinese Office Action mailed on Sep. 26, 2024, issued in Chinese Application No. 2021800308504; 5 pages.
Jiang, Y. et al., "Decreased expression of NR4A nuclear receptors in adenomyosis impairs endometrial decidualization," Molecular Human Reproduction, vol. 22, No .9 pp. 655-668, 2016.
Japanese Office Action mailed on Feb. 12, 2025, issued in Japanese Application No. 2022-550988; 6 pages.
Japanese Office Action mailed on Nov. 18, 2024 issued in Japanese Application No. 2023-118472; 6 pages.
Chinese Notification to Go through Formalities of Registration mailed on Feb. 11, 2025, issued in Chinese Application No. 2021800308504; 6 pages.
Zeng, X. et al., "NR4A1 is Involved in Fibrogenesis in Ovarian Endometriosis," Cell Physiol Biochem 2018;46:1078-1090.
International Search Report mailed on May 6, 2021, issued in corresponding International Application No. PCT/US2021/19402, filed on Feb. 24, 2021, 3 pages.
Written Opinion of the International Searching Authority mailed on May 6, 2021, issued in corresponding International Application No. PCT/US2021/19402, filed on Feb. 24, 2021, 4 pages.
Office Action mailed Jun. 16, 2023, issued in corresponding U.S. Appl. No. 17/510,904, filed Oct. 26, 2021, 47 pages.
Ji, et al. Synlett (2003), (13), 2077-2079 (abstract); Accession No. 2003:865551.
Lin, et al. CN 101979631 (abstract); Feb. 23, 2011; Accession No. 2011 :230668.
Zhang, et al. Synthetic Communications (2011 ), 41 (16), 2446-2454 (abstract); Accession No. 2011:751510.
Zhungietu, et al. Khimiya Geterotsiklicheskikh Soedinenii (1973), (1 ), 40-4 (abstract); Accession No. 1973:111201.
Bharate, et al. European Journal of Medicinal Chemistry (2013), 63, 435-443 (abstract); Accesion No. 2013:892485.
Kumar, K.S., et al., "Micelle Promoted Synthesis of Bis-(indolyl)methanes," Letters in Organic Chemistry, 2012, vol. 9(4), pp. 294-299.
Kim, et al. Bulletin of the Korean Chemical Society (2009), 30(1 ), 197-200. Accession No. 2009:272800.
Nikoofar, et al. Arabian Journal of Chemistry (2019), 12(8), 3776-3784. Accession No. 2016:242202.
Tabatabaeian, et al. Canadian Journal of Chemistry (2006), 84(11 ), 1541-1545. Accession No. 2006: 1261579, retrieved from STN.
Decision of Rejection issued Mar. 22, 2023 in CN Patent App. No. 201880065793.1 filed Aug. 9, 2018.
Decision of Rejection mailed Mar. 20, 2023, in JP Patent App. No. 2020-507693, filed Aug. 9, 2018.
Zoifigol, M.A., et al., "The first urea-based ionic liquid-stabilized magnetic nanoparticles: an efficient catalyst for the Synthesis of bis(indolyl)methanes and pyrano[2,3-d]pyrimidinone derivatives," Applied Organometallic Chemistry, Longman Group UK, Ltd, Hoboken, USA, vol. 30, No. 5, Feb. 4, 2016, pp. 273-281.
Khazaei, A., et al., "Iconic Liquid Tributyl {Carboxymethyl) Phosphonium Bromide as an efficient Catalyst for the Synthesis of bis(indolyl) Methandes under Solvent-Free Conditions," Journal of Chemcial Research, vol. 37, No. 10, Oct. 1, 2013, pp. 617-619.
Shirini, F., et al., "Succinimide-N-sulfonic acid catalyzed synthesis of bis(indolyl)methane and courmarin derivatives under mild conditions," Chinese Journal of Catalysis, vol. 34, No. 10, Oct. 1, 2013, pp. 1890-1896.
Communication pursuant to Article 94(3) EPC for European Application No. 18843948.3 dated Feb. 13, 2023.
Australian Examination Report No. 3, issued Mar. 2, 2023, in AU Application No. 2018313925.
Australian Examination Report No. 4, issued May 8, 2023, in AU Application No. 2018313925, 9 pages.
First Office Action mailed May 30, 2023, issued in corresponding CN Application No. 202080068950.1, filed Jul. 31, 2020, 9 pages.
Li, X., et al., "Structure-dependent activation of gene expression by bis-indole and quinoline-derived activators of nuclear receptor 4A2," Chemical Biology & Drug Design, vol. 94(4), May 18, 2019, pp. 1711-1720.
European Communication Pursuant to Article 94(3) EPC mailed on Jun. 4, 2025, issued in European Application No. 20 846 800.9, filed on Jul. 31, 2020; 5 pages.

(56) References Cited

OTHER PUBLICATIONS

Israeli Notice of Deficiencies mailed on Jun. 9, 2025 in Israel Patent Application No. 295835, filed on Feb. 24, 2021; 3 pages.
Non-Final Rejection mailed on Jun. 5, 2025, issued in U.S. Appl. No. 17/631,390, filed Jan. 28, 2022; 26 pages.
Fu, L.-P. et al., "Three-Component Domino Reactions for Regioselective Formation of Bis-indole Derivatives," ACS Comb. Sci. 2013, 15, 135-140.
Inamoto, T. et al., "1, 1-Bis(3'-indolyl)-1-(p-chlorophenyl)methane activates the orphan nuclear receptor Nurr1 and inhibits bladder cancer growth," Mol Cancer Ther 2008;7 (12). Dec. 2008; pp. 3825-3833.
Jiang, B. and X.-H. Gu, "Syntheses and Cytotoxicity Evaluation of Bis(indolyl)thiazole, Bis(indolyl)pyrazinone and Bis(indolyl)pyrazine: Analogues of Cytotoxic Marine Bis(indole) Alkaloid," Bioorg. Med. Chem. 8 (2000) 363-371.
Halawa, A. H. et al., "Synthesis and biological activities of new bis-indole derivatives via microwave irradiation," Z. Naturforsch. 2017; 72(9)b: 639-646.
Andreani, A. et al., "Antitumor Activity of Bis-indole Derivatives1," J. Med. Chem. 2008, 51. 4563-4570.
Andreani, A. et al., "Antitumor activity and Compare analysis of bis-indole derivatives," Elsevier: Bioorganic & Medicinal Chemistry 18 (2010) 3004-3011.
Amato, J. et al., "Bis-indole derivatives with anitumor activity turn out to be specific ligands of human telomeric G-quadruplex," Frontiers in Chemistry, Jul. 2014, vol. 2, Article 54; pp. 1-8.
Australian Examination Report mailed on Aug. 12, 2025, issued in Australian Application No. 2020320289; 14 pages.
Canadian Office Action mailed on Jul. 31, 2025, issued in Canadian Application No. 3, 149,311; 11 pages.
Kalla, R.M.N; et al. "Synthesis of Bis(indolyl)methanes Using Hyper-Cross-Linked Polyaromatic Spheres Decorated with Bromomethyl Groups as Efficient and Recyclable Catalysts" ACS Omega, 2018, vol. 3, No. 2, pp. 2242-2253, DOI: 10.1021/acsomega.7b01925.
Khatab T.K .; et al. "V2O5 based quadruple nano-perovskite as a new catalyst for the synthesis of bis and tetrakis heterocyclic compounds" Applied Organometallic Chemistry, 2019; vol. 33, e4783; DOI: 10.1002/aoc.4783.
Soliman, H.A.; et al. "An efficient synthesis of bis(indolyl) methanes and N,N'-alkylidene bisamides by Silzic under solvent free conditions" Chinese Chemical Letters, 2016, vol. 27, No. 3, pp. 353-356, DOI: 10.1016/j.cclet.2015.11.013.
Khatab, T.K .; et al. "V2O5/SiO2 as a Heterogeneous Catalyst in the Synthesis of bis(indolyl)methanes Under Solvent Free Condition" Silicon, 2018, vol. 10, pp. 703-708, DOI: 10.1007/s12633-016-9515-8.
Nemallapudi, B.R.; et al. "Meglumine as a green, efficient and reusable catalyst for synthesis and molecular docking studies of bis(indolyl)methanes as antioxidant agents", Bioorganic Chemistry, Jun. 2019, vol. 87, pp. 465-473, DOI: 10.1016/j.bioorg.2019.03.005.
Kalla, R.M.N; et al. "Tetramethyl guanidinium chlorosulfonate as a highly efficient and recyclable organocatalyst for the preparation of bis(indolyl)methane derivatives" Catalysis Communications, 2014, vol. 57, pp. 55-59, DOI: 10.1016/j.catcom.2014.08.003.
Maciejewska D.; et al. "Novel 3,3'-diindolylmethane derivatives: synthesis and cytotoxicity, structural characterization in solid state" European Journal of Medicinal Chemistry, 2009, vol. 44, No. 10, pp. 4136-4147, DOI: 10.1016/j.ejmech.2009.05.011.
Final Office Action mailed on Jan. 8, 2026 in U.S. Appl. No. 17/631,390; 31 pages.
Chang L.-F. et a., "Overexpression of the Orphan Receptor Nur77 and its Translocation Induces by PCH4 May Inhibit Malignant Giloma Cell Growth and Induce Cell Apoptosis," Journal of Surgical Oncology 2011; 103:442-450.
Wilcken, R. et al., "Principals and Applications of Halogen Bonding in Medicinal Chemistry and Chemical Biology," J. Med. Chem. 2013, 56, 1363-1388.

* cited by examiner

METHODS FOR TREATING ENDOMETRIOSIS

CROSS-REFERENCES TO RELATED APPLICATIONS

The present application is a National Stage of International Application No. PCT/US2021/019402, filed on Feb. 24, 2021, which claims the benefit of U.S. Provisional Application No. 62/981,431, filed on Feb. 25, 2020, the content of each of which is incorporated herein by reference in its entirety.

STATEMENT OF GOVERNMENT LICENSE RIGHTS

This invention was made with Government support under P30-ES029067 awarded by National Institutes of Health. The Government has certain rights in the invention.

BACKGROUND

Endometriosis is a common but complex inflammatory disease that primarily affects women during their reproductive years, and it is estimated that 5,500,000 women in the United States and 176,000,000 women worldwide exhibit symptoms of endometriosis. Endometriosis develops when cells lining the uterus are implanted at distal sites which can include the pelvic area, peritoneal surfaces, ovaries, ligaments, bowel, and bladder. Endometriosis originates, in part, from retrograde menstruation; resulting in endometriotic lesions, which are variable to their severity and pain and overall short term or chronic adverse health effects. Once diagnosed, the staging of the disease (i.e., stage I-IV) and its location are important for determining the appropriate treatment regimen which may include surgical removal of the endometriotic tissues and hormonal therapies which include progestins, oral contraceptives, and GnRH antagonists. There are serious concerns regarding the use of hormonal therapies for treating endometriosis in women of childbearing age, and less toxic hormone-independent treatments need to be developed.

There is presently an unmet need for a method of treating endometriosis that avoids or reduces the noted side effects of conventional hormone therapy treatments of endometriosis.

The signaling pathways activated in endometriosis resemble those observed in cancer and include inflammatory-mediated responses associated with macrophage recruitment and activation, activation of growth-promoting and survival genes/pathways, and angiogenic/pro-migration genes/pathways. For example, mTOR signaling is activated in endometriosis. However, the use of mTOR inhibitors for treating this disease is limited due to toxicity concerns.

The orphan nuclear receptors Nuclear Receptor Subfamily 4 Group A Member 1 (NR4A1) (such as according to SEQ ID NO. 1), Nuclear Receptor Subfamily 4 Group A Member 2 (NR4A2), and Nuclear Receptor Subfamily 4 Group A Member 3 (NR4A3) are immediate early genes induced by multiple stressors, and NR4A receptors play an important role in maintaining cellular homeostasis and disease. There is increasing evidence for the role of these receptors in metabolic, cardiovascular and neurological functions as well as in inflammation and inflammatory diseases and in immune functions and cancer. NR4A1 regulates cancer cell proliferation, survival, cell cycle progression, migration, and invasion in lung, melanoma, pancreatic, colon, cervical, ovarian, and gastric cancer, and Rhabdomyosarcoma cell lines and these responses are inhibited by bis-indole derived NR4A1 ligands that act as antagonists in cancer cells.

There is also evidence that NR4A1 is overexpressed in endometriosis, and it was reported that after ultrasound-guided ethanol scleropathy in patients with high serum expression of NR4A1, levels of this receptor were significantly decreased after therapy. Levels of phosphorylated NR4A1 were higher in ovarian endometriotic tissue compared to normal endometrium; moreover, loss of NR4A1 stimulated fibrogenesis and activation of NR4A1 by the NR4A1 agonist cytosporone β suggested this receptor protected against fibrogenesis. Ishikawa endometrial cancer cells are frequently used as models for endometriotic epithelial cells, and our recent study clearly showed that NR4A1 exhibited pro-endometriotic activities that were inhibited by NR4A1 antagonists.

SUMMARY

The present disclosure provides such methods of treating endometriosis along with other related advantages. In this regard, the present disclosure demonstrates that NR4A1 regulates multiple pro-endometriotic genes/pathways that are inhibited by NR4A1 antagonists and, in an aspect, provides methods of treating endometriosis in an individual by modulation of Nuclear Receptor Subfamily 4 Group A Member 1 (NR4A1) activity, comprising administering to the individual a therapeutically effective amount of a compound of the present disclosure, such as an NR4A1 ligand.

In an embodiment, the NR4A1 ligand has the formula:

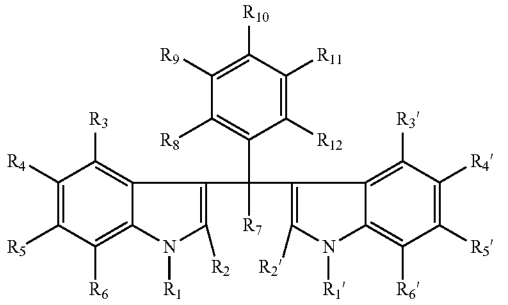

or a salt thereof, wherein, $R_1$, $R_2$, $R_1'$, and $R_2'$ are each independently selected from the group consisting of hydrogen, a linear alkyl group containing one to about ten carbon atoms, and a branched alkyl group containing one to about ten carbon atoms;

$R_3$, $R_4$, $R_5$, $R_6$, $R_3'$, $R_4'$, $R_5'$, and $R_6'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

$R_7$ is selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

$R_8$, $R_9$, $R_{10}$, $R_{11}$, and $R_{12}$ are independently selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a hydroxyl group, and a haloalkoxy group containing one to about ten carbon atoms;

wherein at least one of $R_8$, $R_9$, $R_{10}$, $R_{11}$, and $R_{12}$ is OH, and wherein when $R_{10}$ is OH at least one of $R_8$, $R_9$, $R_{11}$, and $R_{12}$ is not hydrogen.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspect and many of the attendant advantages of claimed subject matter will become more readily appreciated as the same become better understood by reference to the following detailed description, when taken in conjunction with the accompanying drawings, wherein:

DETAILED DESCRIPTION

Figure 1A:
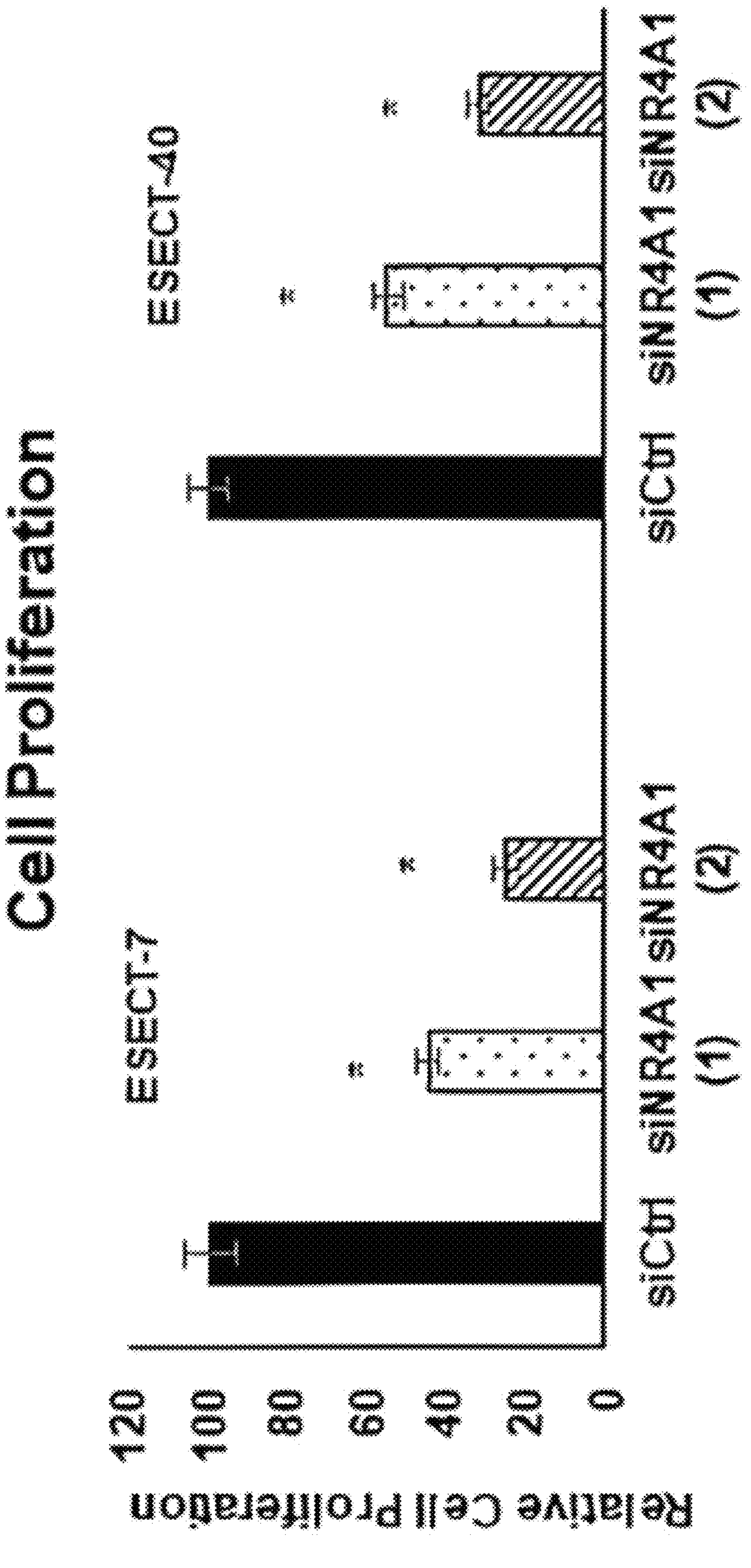
FIGS. 1A-1D illustrate the effects of NR4A1 knockdown in endometriotic cells where ESECT-7 and ESECT-40 cells were transfected with oligonucleotides targeting downregulation of NR4A1 [siNR4A1 (1) and siNR4A1 (2)] and effects on cell proliferation (1A), NR4A1 expression (1B), growth promoting (1C) and proapoptotic (1D) gene products are shown, in accordance with an embodiment of the disclosure.

Endometriosis is an inflammatory disease that primarily affects women during their reproductive years and since current hormonal therapies are of concern new hormone-independent treatment regimens are needed. The orphan nuclear receptor 4A1 (NR4A1, Nur77), such as according to SEQ ID NO. 1, is expressed in patient-derived (stromal) endometriotic cells and also epithelial cell lines, and present disclosure demonstrates that knockdown of NR4A1 in patient-derived ESECT-7 and ESECT-40 cells decreased cell proliferation and induced apoptosis. Moreover, the treatment of these cells with bis-indole derived NR4A1 ligands 1,1-bis(3'-indolyl)-1-(p-hydroxyphenyl)methane (DIM-C-pPhOH) and its buttressed 3-chloro-5-methoxy analog (DIM-C-pPhOH-3-Cl-5-OCH3) inhibited cell growth and induced apoptosis and related genes. The compounds of the present disclosure exhibit NR4A1 antagonist activities in both functional and transactivation assays whereas these effects were not observed in normal (NEM) endometrial cells. The present disclosure also demonstrates that NR4A1 knockdown and treatment with NR4A1 antagonists decreased fibrosis, α-smooth muscle actin (α-SMA), and related pro-fibrotic genes in ESECT-7 and ESECT-40 cells, and similar results were observed in epithelial-derived endometriotic cell lines. Moreover, in an endometriosis mouse model with auto-transplantation and, also, in SCID mice transplanted with human endometriotic cells treatment with 25 mg/kg/day DIM-C-pPhOH-3-Cl-5-OCH3 significantly inhibited growth and expansion of endometriotic lesions. Thus, the present disclosure demonstrates that bis-indole derived NR4A1 ligands are a novel class of drugs for non-hormonal therapy for endometriosis.

Accordingly, in an aspect, the present disclosure provides methods of treating endometriosis. In an embodiment, the methods include treating endometriosis in an individual treatable by modulation of NR4A1 activity, comprising administering to the individual a therapeutically effective amount of a compound, such as a NR4A1 ligand. In an embodiment, the compound is a methylene substituted diindolylmethane. In certain embodiments, compounds according to the present disclosure are variously referred to "CDIM" or "C-DIM" compounds. As discussed further herein, in certain embodiments, such compounds are methylene substituted diindolylmethane compounds, such as according to the chemical formulas according to embodiments of the present disclosure.

In some embodiments, modulating NR4A1 activity comprises the binding of a compound described elsewhere herein to the NR4A1 protein. In some embodiments, the compound has antagonistic activity, namely the compound has reduced or no efficacy in stimulating the cognate function of the receptor (e.g., an antagonist ligand). In some embodiments, the antagonist ligand blocks the constitutive function of the receptor and its ability for stimulatory, cognate ligands to bind to the NR4A1 protein and to activate NR4A1-dependent genes. In some embodiments, the NR4A1 ligand can be a tissue-, response-, or gene-specific agonist. In an embodiment, the NR4A1 ligand is effective in endometriotic cells of the individual. Such endometriotic cells are in contrast to normal endometriotic (NEW) cells of the individual.

The term "antagonist" refers to a compound that can combine with a NR4A1 receptor to reduce or inhibit a molecular and cellular activity. An antagonist may be a ligand that directly binds to the receptor. Alternatively, an antagonist may combine with a receptor indirectly by, for example, (a) forming a complex with another molecule or protein that directly binds to the receptor, or (b) otherwise results in the modification of another compound so that the other compound directly binds to the NR4A1 receptor.

The term "agonist" refers to a compound that can combine with a NR4A1 receptor to produce or increase a molecular and cellular activity. An agonist may be a ligand that directly binds to the receptor. Alternatively, an agonist may combine with a receptor indirectly by, for example, (a) forming a complex with another molecule or protein that directly binds to the receptor, or (b) otherwise results in the modification of another compound so that the other compound directly binds to the NR4A1 receptor.

The term "activate", and variations thereof, refers to any measurable increase in molecular and cellular activity.

In an embodiment, the cell is contacted with the compound or pharmaceutical composition in vitro. In an embodiment, the cell is contacted with the compound or pharmaceutical composition in vivo by administering an effective amount of the compound or pharmaceutical composition to a subject.

Figures 6A, 6B:
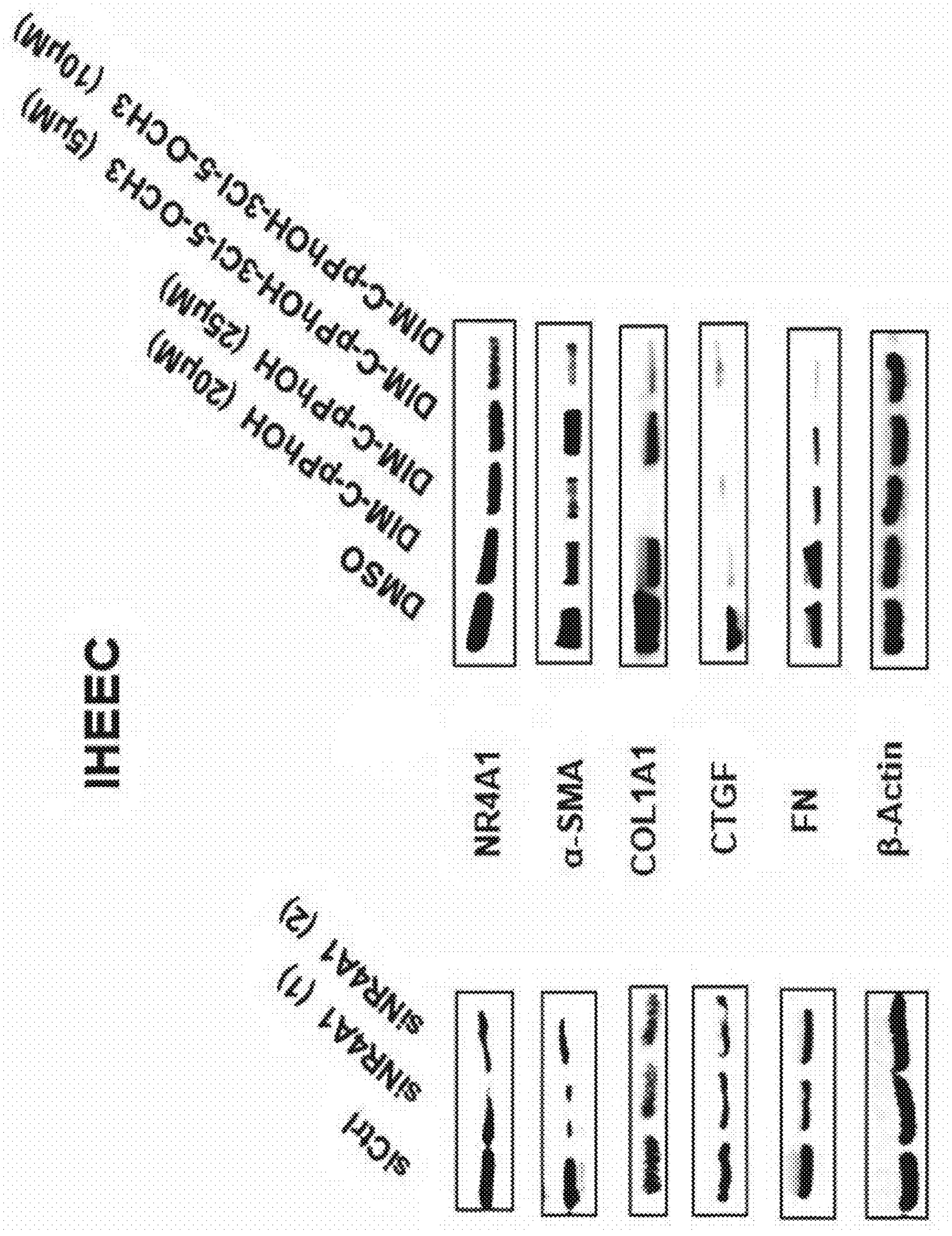
FIGS. 6A and 6B illustrate the effects of NR4A1 antagonists and receptor knockdown on IHEEC cells transfected with siNR4A1 oligonucleotides (6A) or treated for 24 hours with NR4A1 antagonists (6B), in accordance with an embodiment of the disclosure.

In an embodiment, modulation of NR4A1 induces down-regulation of a protein selected from the group consisting of EFGR, cMyc, survivin, Bcl-2, SMA, and combinations thereof. As shown in, for example, EXAMPLES 2 and 3 and FIGS. 1C, 1D, 2D, and 3C, the compounds of the present disclosure when administered to a subject are suitable to induce down-regulation of EFGR, cMyc, survivin, Bcl-2, such as in endometriotic cells and relative to a control. In an embodiment, EFGR is according to SEQ ID NO. 2. In an embodiment, cMyc is according to SEQ ID NO. 3. In an embodiment, survivin is according to SEQ ID NO. 4. In an embodiment, Bcl-2 is according to SEQ ID NO. 5. As shown, for example, EXAMPLE 4 and FIG. 6B, the compounds of the present disclosure are suitable to induce down-regulation of SMA, such as in endometrial cells and relative to a control. In an embodiment, SMA is according to SEQ ID NO. 6.

In an embodiment, modulation of NR4A1 activity induces up-regulation of a protein including Bax. As shown in, for example, EXAMPLES 2 and 3 and FIGS. 1C, 1D, 2D, and 3C, the compounds of the present disclosure when administered to a subject are suitable to induce up-regulation of Bax, such as in endometriotic cells and relative to a control. In an embodiment, Bax is according to SEQ ID NO. 7.

In an embodiment, modulation of NR4A1 activity induces decreased level of mRNA levels of fibrosis markers selected from the group consisting of FN, Col1A1, CTGF, and combinations thereof. As shown in, for example, EXAMPLE 4 and FIG. 6B, the compounds when administered to a subject are suitable to induce decreased levels of mRNA levels of fibrosis markers such as FN, Col1A1, CTGF, such as in endometriotic cells and relative to a control. In an embodiment, FN is according to SEQ ID NO. 8. In an embodiment, Col1A1 is according to SEQ ID NO. 9. In an embodiment, CTGF is according to SEQ ID NO. 10.

In an embodiment, modulation of NR4A1 activity cleaves PARP and caspase-3. As show, the compounds according to the present disclosure are suitable to induce cleavage of PARP and caspase-3 when administered to a subject, such as in endometriotic cells and relative to a control. In an embodiment, PARP is according to SEQ ID NO. 11. In an embodiment, caspase-3 is according to SEQ ID NO. 12.

While particular embodiments of proteins are described, it will be understood that other homologs or isoforms of these proteins are within the scope of the present disclosure.

In an embodiment, modulation of NR4A1 activity induces apoptosis in ovarian endometrioma.

In an embodiment, modulation of NR4A1 activity does not inhibit growth of normal endometrial cells relative to a control.

In an embodiment, modulation of NR4A1 activity inhibits progression of fibrosis, such as relative to a control.

In an embodiment, modulation of NR4A1 activity suppresses intrinsic transcriptional activity of NR4A1 in endometriotic cells relative to a control. In an embodiment, modulation of NR4A1 activity suppresses growth of ectopic lesions relative to a control.

In an embodiment, the NR41 ligands of the present disclosure are according to the following formula:

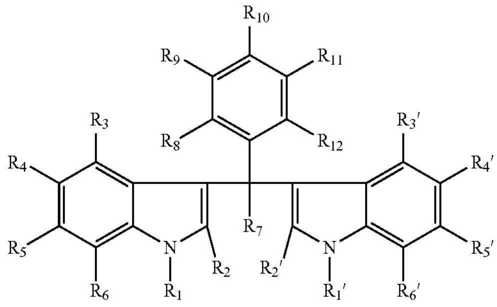

or a salt thereof, wherein, $R_1$, $R_2$, $R_1'$, and $R_2'$ are each independently selected from the group consisting of hydrogen, a linear alkyl group containing one to about ten carbon atoms, and a branched alkyl group containing one to about ten carbon atoms;

$R_3$, $R_4$, $R_5$, $R_6$, $R_3'$, $R_4'$, $R_5'$, and $R_6'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

$R_7$ is selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

$R_8$, $R_9$, $R_{10}$, $R_{11}$, and $R_{12}$ are independently selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a hydroxyl group, and a haloalkoxy group containing one to about ten carbon atoms;

wherein at least one of $R_8$, $R_9$, $R_{10}$, $R_{11}$, and $R_{12}$ is OH, and wherein when $R_{10}$ is OH at least one of $R_8$, $R_9$, $R_{11}$, and $R_{12}$ is not hydrogen.

Chemical moieties referred to as univalent chemical moieties (e.g., alkyl, aryl, and the like) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —$CH_2CH_2$—, which is equivalent to an "alkylene" group). Similarly, under circumstances where a divalent moiety is required, those skilled in the art will understand that the term "aryl" refers to the corresponding divalent arylene group.

Terms used herein may be preceded and/or followed by a single dash, "—", or a double dash, "═", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly, arylalkyl and -alkylaryl indicate the same functionality.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, and the like), the number of repeated atoms or groups can be represented by a range (e.g., $C_1$-$C_6$ alkyl) which includes each and every number in the range and any and all sub ranges. FOE example, $C_1$-$C_3$ alkyl includes $C_1$, $C_2$, $C_3$, $C_{1-2}$, $C_{1\_3}$, and $C_{2\_3}$ alkyl.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3).

"Alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocycle heterocyclyl portions of the bicyclic aryl are optionally substituted with one or two oxo and/or this group.

"Halogen" refers to a chloro, bromo, fluoro or iodo atom radical. The terra "halogen" also contemplates terms "halo" or "halide".

The terms "haloalkyl", "haloalkenyl" and "haloalkoxy" refer to an alkyl, alkenyl or alkoxy group, as the case may be, which is substituted with one or more halogen atoms.

The term "nitro" as used herein, means a —$NO_2$ group.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

In an additional embodiment, the present disclosure pertains to methods of treating endometriosis in an individual by modulation of NR4A1 that include administering a bis-indole-derived compound, as described in WO2021/022220, to a subject in need thereof. The disclosure of WO2021/022220 is hereby incorporated herein by reference for its disclosure. In some embodiments, the method further includes binding, by the bis-indole-derived compound, to at least one of nuclear receptor 4A1 (NR4A1) and nuclear receptor 4A2 (NR4A2). In some embodiments, the bis-indole-derived compound (CDIM) includes two or more substituents on a phenyl ring thereof. In some embodiments, the bis-indole-derived compound includes, without limitation, 1,1-bis(3'-indolyl)-1-(p-chlorophenyl)methane (DIM-C-pPhCl; 4-Cl), 1,1-bis(3'-indolyl)-1-(4-chloro-3-trifluoromethylphenyl)methane (3-$CF_3$-4-Cl), 1,1-dimethyl-1,1-bis(3'-indolyl)-1-(p-hydroxyphenyl)methane (N-Me-4-OH), 1,1-bis(3'-indolyl)-1-(4-bromo-2-hydroxy-phenyl)methane (2-OH-4-Br), 1-bis(3'indolyl)-1-(p-bromophenyl)methane (DIM-C-pPhBr), 1,1-bis(3'-indolyl)-1-(p-hydroxyphenyl) methane (CDIM8), a 3,5-disubstituted analog of CDIM8, CDIM8-3,5-($CH_3$)2, CDIM8-3,5-$Br_2$, CDIM8-3,5-$Cl_2$, CDIM8-3-Br-5-$OCH_3$, CDIM8-3-Cl-5-$OCH_3$, CDIM8-3-Cl-5-Br, CDIM8-3-Cl-5-F, CDIM, a 3,5-disubstituted analog of CDIM, CDIM-3,5-$Br_2$, CDIM-2,5-$Br_2$, CDIM-3,5-$Cl_2$, CDIM-3,5-(CH3)2, CDIM-3-Br-5-$OCF_3$, CDIM-3-Br-5-$OCH_3$, CDIM-3-Br-5-$CF_3$ CDIM-3-Cl-5-$OCH_3$, CDIM-3-Cl-5-$OCF_3$, CDIM-3-Cl-5-$CF_3$, and combinations thereof. In an embodiment, the bis-indole-derived compound is CDIM-3-Br-5-$CF_3$.

2-Hydroxy Ligands

In some embodiments, $R_8$ is OH. In certain instances, such ligands are referred to herein as "2-hydroxy" and/or "2-OH" ligands due to the placement of the OH group on the central phenyl group. In certain such embodiments, $R_9$, $R_{10}$, $R_{11}$, and $R_{12}$ are each H. In certain other embodiments, $R_9$, $R_{10}$, $R_{11}$, and $R_{12}$ are independently selected from the group consisting of a halogen, $CH_3$, $OCCl_3$, $CF_3$, t-butyl, $OCH_3$, OH, $C_6H_5$, and CN. In an embodiment, $R_{10}$ is $OCH_3$. In an embodiment, $R_{11}$ is selected from the group consisting of $CH_3$, $OCH_3$, and $CF_3$. In an embodiment, $R_9$ and $R_{11}$ are Br.

In an embodiment, the compositions of the disclosure have one of the following structures:

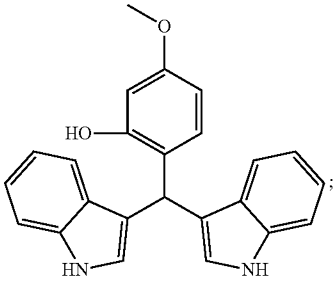
;

-continued

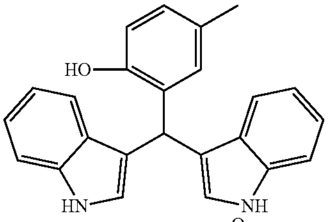
;

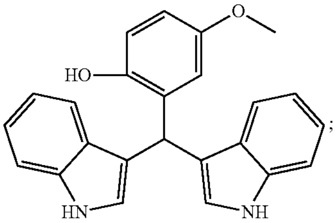
;

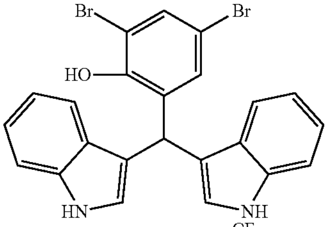
;

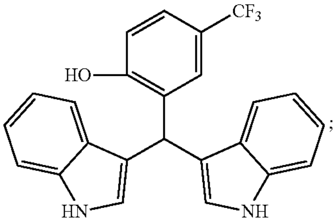
;

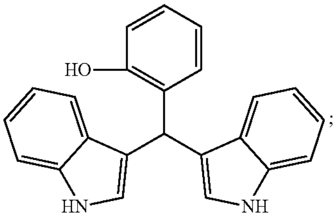
;

and salts thereof.

3-Hydroxy Ligands

In some embodiments, $R_9$ is OH. In certain instances, such ligands are referred to herein as "3-hydroxy" and/or "3-OH" ligands due to the placement of the OH group on the central phenyl group. In certain such embodiments, $R_8$, $R_{10}$, $R_{11}$, and $R_{12}$ are each H. In certain other embodiments, $R_8$, $R_{10}$, $R_{11}$, and $R_{12}$ are independently selected from the group consisting of a halogen, $CH_3$, $OCCl_3$, $CF_3$, t-butyl, $OCH_3$, OH, $C_6H_5$, and CN. In certain embodiments, $R_8$ is a halogen.

In an embodiment, the compositions of the disclosure have one of the following structures:

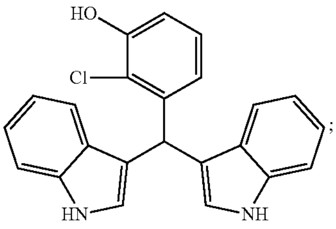
;

-continued

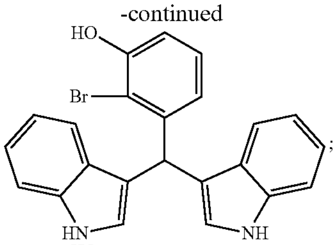

;

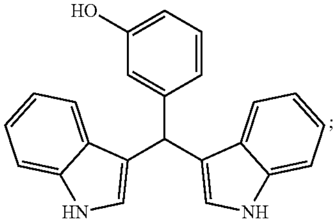

;

and salts thereof.

4-Hydroxy Ligands

In some embodiments, $R_{10}$ is OH. In certain instances, such ligands are referred to herein as “4-hydroxy” and/or “4-OH” ligands due to the placement of the OH group on the central phenyl group. In certain such embodiments, $R_8$, $R_9$, $R_{11}$, and $R_{12}$ are independently selected the group consisting of a halogen, $CH_3$, $OCCl_3$, $CF_3$, t-butyl, $OCH_3$, OH, $C_6H_5$, and CN. In certain other embodiments, $R_9$ is a halogen and $R_{11}$ is selected from the group consisting of H, a halogen, and $OCH_3$.

In an embodiment, the compositions of the disclosure have one of the following structures:

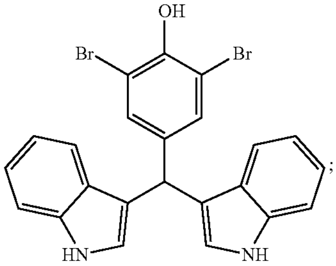

;

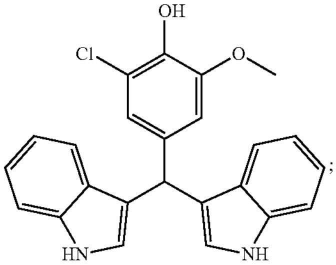

;

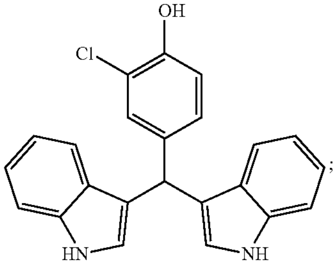

;

and salts thereof.

The C-DIM compounds of the present disclosure can be prepared by condensation of substituted benzaldehydes with indole or substituted indoles. The compounds can be synthesized by incubating two parts indole or substituted indole with one-part benzaldehyde or substituted benzaldehyde in dilute acetic acid at 80-90° C. for 24-48 hours. The solid is recovered by filtration and crystalized from benzene or benzene/hexane to give a 70-90% yield of C-DIM. Use of a single indole starting material will lead to symmetrical products, while use of two different indole starting materials will lead to asymmetrical products.

The preparation and characterization of representative C-DIM compounds is described, for example, in U.S. Pat. No. 7,232,843, incorporated herein by reference in its entirety.

Those having ordinary skill in the art will be able to ascertain the most effective dose and times for administering the compositions, considering route of delivery, metabolism of the compound, and other pharmacokinetic parameters such as volume of distribution, clearance, age of the subject, and so on. For example, an NR4A1 ligand, such as an NR4A1 antagonist, can be administered in any well-known method, such as by topical administration, oral administration, intravenous injection, intraperitoneal injection, intramuscular injection, intranasal administration, transdermal administration, rectal administration, or by any means which delivers an effective amount of the active agent to the tissue or site to be treated. Suitable dosages are those which achieve the desired endpoint. It will be appreciated that different dosages may be required for treating different disorders. An effective amount of an agent is, for example, that amount which causes a cessation or significant decrease in neoplastic cell count, growth, size, cell migration or cell invasion.

The compositions can be administered along with a pharmaceutical carrier and/or diluent. The agents may also be administered in combination with other agents, for example, in association with other compounds suitable for the treatment of endometriosis. Examples of pharmaceutical carriers or diluents useful in the present invention include any physiological buffered medium, i.e., about pH 7.0 to 7.4 comprising a suitable water-soluble organic carrier. Suitable water-soluble organic carriers include, but are not limited to corn oil, dimethylsulfoxide, gelatin capsules, and so on.

The term “therapeutically effective amount” used herein refers to an amount of a compound or composition sufficient to treat a specified disorder, condition or disease such as ameliorate, palliate, lessen, and/or delay one or more of its symptoms. In reference to endometriosis or other unwanted cell proliferation, an effective amount comprises an amount sufficient to cause a endometriotic lesion to shrink and/or to decrease the growth rate of the endometriotic lesions. In some embodiments, an effective amount is an amount sufficient to delay development. In some embodiments, an effective amount is an amount sufficient to prevent occurrence and/or recurrence. An effective amount can be administered in one or more administrations.

“Pharmaceutically acceptable carriers” for therapeutic use are well known in the pharmaceutical art, and are described, for example, in Remington’s Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sortie acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable, and which provides the formulation with the desired pH, i.e., a pH in the physiologically acceptable range. Examples of buffer solutions include saline, phosphate buffered saline, Tris buffered saline, Hank's buffered saline and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

The disclosure includes a pharmaceutical composition comprising a compound of the disclosure including isomers, racemic or non-racemic mixtures of isomers, or pharmaceutically acceptable salts or solvates thereof together with one or more pharmaceutically acceptable carriers, and optionally other therapeutic and/or prophylactic ingredients.

In general, the compounds of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the disclosure for a given disease.

Thus, the compounds of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); poly-anions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compounds of the disclosure can be combined with an oral, nontoxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Thus, for example, capsules can be prepared by conventional procedures so that the dosage unit is 100 mg of the compounds of the disclosure, 100 mg of cellulose and 10 mg of magnesium stearate. A large number of unit capsules can also be prepared by filling standard two-piece hard gelatin capsules each with 100 mg of powdered active ingredient, 150 mg of lactose, 50 mg of cellulose, and 10 mg magnesium stearate. Or, tablets can be prepared by conventional procedures so that the dosage unit is 100 mg of the compounds of the disclosure, 150 mg of lactose, 50 mg of cellulose and 10 mg of magnesium stearate. A large number of tablets can also be prepared by conventional procedures such that the dosage unit was 100 mg of the compounds of the disclosure, and other ingredients can be 0.2 mg of colloidal silicon dioxide, 5 mg of magnesium stearate, 250 mg of microcrystalline cellulose, 10 mg of starch and 100 mg of lactose. Appropriate coatings can be applied to increase palatability or delay absorption.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms sinkable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered liming a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, suede, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria-retaining filter, by incorporating sterilizing agents into the composition, by irradiating the compositions, or by heating the compositions. They can also be manufactured using sterile water, or some other sterile injectable medium, immediately before use.

The formulations can optionally contain an isotonicity agent. The formulations preferably contain an isotonicity agent and glycerin is the most preferred isotonicity agent. The concentration of glycerin, when it is used, is in the range known in the art, such as for example, about 1 mg/mL to about 20 mg/mL.

The pH of the parenteral formulations can be controlled by a buffering agent such as phosphate, acetate, TRIS or L-arginine. The concentration of the buffering agent is preferably adequate to provide buffering of the pH during storage to maintain the pH at a target pH±0.2 pH unit. The preferred pH is between about 7 and about 8 when measured at room temperature.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) can optionally be added to the formulation, and can be useful if the formulations will contact plastic materials. In addition, the parenteral formulations can contain various antibacterial and antifungal agents, for example, parabens, chlorobutanol, phenol, sorbic acid, thimerosal, and the like.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmuscosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compounds of the disclosure can be formulated for aerosol administration, particularly to the respiratory tract and including intranasal administration. The compound will generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dosing can be controlled by a metered valve. Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the disclosure, generally a therapeutic amount will be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself or it can be the appropriate number of any of these in packaged form.

The individual can be any animal, such as a mammal, bird, reptile, or fish. Exemplary mammalian categories include rodents, primates, canines, felines, ungulates, lagomorphs, and the like. For example, the individual can be a human, monkey, ape or other primate, mouse, rat or other rodent, dog, cat, pig, horse, cow, or rabbit, etc.

As used herein, the term "treatment" means providing an ameliorative, curative, or preventative effect on the disorder or condition. In some embodiments, treatment includes preventing the escalation or progression, or slowing the rate of escalation or progression, of the condition (as compared to no or other treatment). In the context of endometriosis (more described below), treatment includes slowing or preventing the cell growth or rate of cell division, slowing or preventing cell migration, and/or slowing or preventing cell invasion. In an embodiment, treatment of endometriosis includes reducing a volume of ectopic lesions and/or suppressing a growth rate of ectopic lesions.

As shown in the EXAMPLES and FIGURES of the present disclosure, the C-DIM/NR4A1 antagonists of the present disclosure suppressed the growth of ESECT-7 and ESECT-40 cells isolated from ovarian endometrioma by activating apoptosis, but do not inhibit the growth of NEM (normal) endometrial cells even though NR4A1 was expressed in NEM cells, in accordance with an embodiment of the present disclosure. In contrast with endometriotic cells, DIM-C-pPhOH and DIM-C-pPhOH-3-Cl-5-OCH3 worked as NR4A1 agonists to induce genes involved in glucose uptake process in C2C12 muscle cells. These cellular differences in the activity of CDIM/NR4A1 ligands (e.g.: antagonist/agonist/inactive) are typically observed for selective receptor modulators that exhibit tissue/cell-specific activities suggesting that the CDIMs are selective NR4A1 modulators. The selectivity of these compounds in their effectiveness in endometriotic but not normal endometrium cells may be due to several reasons including the differential expression of essential cofactors and these are currently being investigated.

The development of fibrosis can lead to decreased fertility and pain during endometriosis. Zeng and coworkers revealed that the knockdown of NR4A1 in normal endometrial tissues (NESCs) and endometriotic tissue (EESCs) enhanced fibrosis and cytosporone β (NR4A1 agonist) treatment inhibited TGFβ-induced fibrosis in NESC and EESC cells. Zeng et al., Cell Physiol Biochem. 2018; 46(3):1078-90. In contrast to this observation, the knockdown of NR4A1 or treatment with C-DIM (NR4A1 antagonists) inhibited the fibrosis progression of ESECT-7 cells and IHEECs as compared to their controls, in accordance with an embodiment of the present disclosure. In the endometriosis mouse model, the present disclosure demonstrates higher levels of NR4A1 in endometriotic tissue compared to normal endometrial tissue, and DIM-C-pPhOH-3-Cl-5-OCH3 treatment suppressed the endometriosis progression in mouse with endometriosis without any changes in body weight, and similar results were observed in SCID mice bearing HECs. Why are there apparently conflicting reports on the role of NR4A1 on endometriosis?Firstly, the Zeng group induced endometriosis into Nr4a1 total KO mice by auto-transplantation of Nr4a1 KO uterine fragments. Therefore, we cannot determine the function of NR4A1 in ectopic lesions for endometriosis progression due to the interference of whole-body Nr4a1 KO female recipients, as described by the Zeng group. In the SCID mouse model, the Zeng group treated mice with 17-β estradiol to stimulate endometriosis progression. However, 17-β estradiol was not injected into recipient mice in the EXAMPLES of the present disclosure. The high concentration of exogenous 17-β estradiol exposure significantly changes intracellular signaling in SCID mice compared to non-treated SCID mice. Without wishing to be bound by theory, it is believed that this type of experimental difference changes the effects of NR4A1 in endometriosis progression.

In summary, the present disclosure demonstrates that NR4A1 is a new pro-endometriotic transcription factor that stimulates progression of endometriosis, and the bis-indole derived NR4A1 antagonists of the present disclosure can be employed as new non-hormonal therapy for endometriosis treatment and such treatment methods minimize or eliminate the side-effects of conventional hormonal therapies.

EXAMPLES

Example 1: Materials and Methods

Primary human endometriotic stromal cells from endometriosis patients: Ovarian endometrioma were isolated from endometriosis patients in the proliferative phase following the IRB-approved protocol. Isolated ectopic lesions were digested with collagenase type 3 (300 μg/ml) and DNaseI (40 μg/ml) for 90 min at 37° C., and then tissues were filtered through 150, 100, and 40 μm sieves to isolate endometrial stromal cells. The collected endometrial stromal cells were cultured in DMEM/F12 with 10% FBS plus 1× antibiotic/antimycotic solution and then validated by flow cytometry with a CD90 antibody (a mesenchymal marker). Henceforth, we refer to the stromal cells as ectopic endometrium isolated ovarian endometrioma (ESECT). As the control, primary normal endometrial stromal cells isolated from the biopsy of the eutopic endometrium of normal women (NEM) in the proliferative phase. All cells were incubated at 37° C. in $CO_2$ incubator in an atmosphere of humidified 5% $CO_2$ and 95% air.

Reagents and Antibodies: Annexin V Dead Cell Apoptosis Kit (V13241) was purchased from Invitrogen. The primary antibodies used were EGFR (4267, 1:1000), Survivin (2808, 1:1000), c-Caspase-3 (9661, 1; 1000), c-PARP (9541, 1:1000) from Cell Signaling Technology (Danvers, MA) and c-Myc (sc-40, 1:500), Bcl-2 (sc-509, 1:500) and Bax (sc-20067, 1:500) from Santacruz Biotechnology (Santacruz, CA), NR4A1 (ab109180, 1:3000) and α-SMA (ab32575, 1:3000) from Abcam (Cambridge, MA), β-Actin (A1978, 1:10000) from Sigma Aldrich Corporation (Milwaukee, WI). COL1A1 (GTX112731, 1:2000), CTGF (GTX124232, 1:2000) and FN (GTX112794, 1:2000) from GeneTex, Inc. (Irvine, CA). Secondary antibodies for rabbit (7074), mouse (7076) and Anti-rabbit Alexa Fluor (4412) purchased from Cell Signaling Technology (Danvers, MA). Two siNR4A1 oligonucleotides used in this study were SASI_Hs02_00333289 and SASI_Hs02_00333290 and nontargeted scrambled small interfering RNA (iGL2) were used as a control from Sigma Aldrich Corporation (The Woodlands, TX). The bis-indole-derived NR4A1 ligands 1,1-bis(3'-indolyl)-1-(p-hydroxyphenyl)methane (DIM-C-pPhOH), 1,1-bis(3'-indolyl)-1-3-chloro-5-methoxyphenyl) methane (DIM-C-pPhOH-3-Cl-5-OCH3), 1,1-bis(3'-indolyl-1-(3,5-dibromo-4-hydroxyohenyl)methane (DIMC-C-pPhOH-3,5-Br2) and 1,1-bis(3'-indolyl)-1-(3-chloro-4-hydroxyphenyl)methane (DIM-C-pPhOH) were prepared as described.

Cell proliferation assay: Patient-derived endometriotic cells ESECT-7 and ESECT-40 were seeded into a 96-well plate, and the cells were then treated for 24 hr with either DMSO or different concentrations of DIM-C-pPhOH and DIM-C-pPhOH-3-Cl-5-OCH3. The ESECT-7 and ESECT-40 were treated with two siNR4A1 oligonucleotides to downregulate NR4A1. Non-target siRNAs were employed as the control of siRNA. Afterward, the medium was removed, and the MTT solution diluted in PBS was added to cell cultures. After 3 hr incubation, the medium was aspirated and washed with PBS. Dimethyl sulfoxide (DMSO) was added and incubated at 370 for 10 min, and absorbance was measured at 570 nM.

Western Blotting: ESECT-7 and ESECT-40 cells (2×105) were seeded and allowed to attach for 24 hr, and cells were then treated for 24 hr with either DMSO or different concentrations of DIM-C-pPhOH and DIM-C-pPhOH-3-Cl-5-OCH3. Cells were then lysed and whole-cell lysates were resolved in 10% SDS-PAGE gels and proteins were transferred using PVDF membrane by wet blotting followed by primary and secondary antibody incubation and detected using ECL reagent as described.

Annexin V staining: ESECT-7 and ESECT-40 cells were seeded in Nunc chambered cover glass followed by various drug treatments. The cells were then washed with ice-cold PBS, and 5 μL Alexa Fluor® 488 Annexin V with 100 μg/mL PI (as per the manufacturer's instructions) were added to the cells and incubated for 15 min, and the cells were observed using a Zeiss confocal fluorescence microscope.

Immunofluorescence: ESECT-7 and ESECT-40 cells were seeded in Nunc chambered cover-glass followed by various drug treatments. The cells were fixed with 4% paraformaldehyde in PBS for 20 minutes at 37° C. Cells were then blocked and incubated overnight with primary α-SMA antibody in the buffer (5% bovine serum albumin in PBS) at 4° C., followed by incubation with Alexa Fluor conjugated secondary antibody at a dilution of 1:250 for 2 hours at room temperature. Finally, cells were observed using a Zeiss confocal fluorescence microscope.

RNA Interference: ESECT-7 and ESECT-40 cells were seeded in six-well plates and allowed to grow to 60% confluence (24 hours), then transfections were performed with Lipofectamine 2000 according to the manufacturer's protocol. Both siNR4A1 oligonucleotides and nontargeted control small interfering RNAs were used. Six hours after transfection, the medium was replaced with fresh medium and left for 72 hours, and the cells were harvested, and protein expression was determined.

Quantitative real-time PCR: Total RNA was isolated from cultured cells according to the manufacturer's instructions (Zymo Research, Irvine, CA). The concentration and purity of the RNA samples were determined using a nanodrop spectrophotometer. Total RNA was reverse transcribed using iTaq Universal SYBR Green One-Step Kit (Thermo Fisher Scientific, Grand Island, NY) using the manufacturer's protocol with the CFX384 real-time PCR System (Bio-Rad). The comparative cycle threshold method was used for relative quantitation of samples. Values for each gene were normalized to expression levels of TATA-binding protein. The sequences of the primers used for real-time PCR included the following: α-SMA, 5'-GGC CGA GAT CTC ACT GAC TAC-3' (sense, SEQ ID NO. 13) and 5'-TTC ATG GAT GCC AGC AGA-3' (antisense, SEQ ID NO. 14); COL1A1, 5'-CAG CCG CTT CAC CTA CAG C-3' (sense, SEQ ID NO. 15) and 5'-TTT TGT ATT CAA TCA GTG TCT TGC C-3' (antisense, SEQ ID NO. 16); CTGF, 5'-TTG GCC CAG ACC CAA CTA TG-3'(sense, SEQ ID NO. 17) and 5'-CAG GAG GCG TTG TCA TTG GT-3' (antisense, SEQ ID NO. 18); FN, 5'-GGG AGC CTC GAA GAG C-3' (sense 19) and 5'-AAC AAG TAC AAA CCA ACG CA-3' (antisense, SEQ ID NO. 20) and TATA-binding protein, 5'-GAT CAG AAC AAC AGC CTG CC-3' (sense, SEQ ID NO. 21) and 5'-TTC TGA ATA GGC TGT GGG GT-3' (antisense, SEQ ID NO. 21).

Luciferase assay: ESECT-7 and ESECT-40 cells were plated on 12-well plates in DMEM/F12 supplemented with 2.5% charcoal-stripped FBS. After overnight attachment and growth, various amounts of DNA [i.e., UASx5-Luc (500 ng), GAL4-NR4A1 (50 ng), NBREx3-Luc (800 ng), NurREx3-Luc (800 ng) and Flag-NR4A1 (80 ng)] were co-transfected into each well using Lipofectamine 2000 reagent (Invitrogen, Carlsbad, CA) according to the manufacturer's protocol. After 6 hr of transfection, cells were treated with plating medium (as above) containing either solvent (DMSO) or indicated concentrations of the compound for 18 hr. Cells were then lysed and cell extracts were used for chemiluminescence quantification of luciferase activity. Luciferase activity values were normalized against corresponding protein concentration values determined by Bradford assay. Both GAL4- and Flag-NR4A1 constructs contain full-length NR4A1 coding sequence and all the plasmids used in this study were previously described.

Endometriosis Mouse Model with Auto-transplantation: One uterine horn was isolated from a female mouse (6 weeks old, C57BL/6J) under anesthesia, and then the uterine horn was longitudinally cut. Using a 2-mm dermal biopsy punch, one endometrial fragment was obtained from the isolated uterus and subsequently sutured to the mesenteric membrane attached to the intestine of the same mouse. The abdominal incision then was closed by suture. Before harvesting ectopic lesions, the mouse estrous cycle was determined using vaginal cytology. At the estrus stage in the 3rd week after endometriosis induction, ectopic lesions were isolated from mice with endometriosis. As the endometriosis control, uteri were isolated from C57BL/6J female mice without endometriosis at the estrus stage at 10 weeks of age.

Endometriosis Mouse Model by Hetero-transplantation with immortalized human endometrial cells: The luciferase stable immortalized human endometrial epithelial cells (LIHESCs) and luciferase stable immortalized human endometrial stromal cells (LIHESCs) were generated from IHESCs isolated from endometria obtained from hysterectomies for benign conditions and IHEECs generated from ovarian endometrioma by transducing lentivirus-expressing luciferase and then the expression of luciferase was validated with the luciferase activity assay. Matrigel contained the mixture of LIHESCs (1×106 cells) and LIHEECs (1×106 cells) were injected into the peritoneal cavity of female severe combined immune deficiency (SCID) mice (6 weeks old) to induce endometriosis. Henceforth, we refer to the mixture of LIHEECs and LIHESCs as human endometrial cells (HEC). The ectopic lesions were well developed in ~80% of the HEC-transplanted SCID mice, and immunostaining with antibodies against vimentin and cytokeratin 18 revealed that ectopic lesions were successfully developed from the HECs. To noninvasively determine the progression of human ectopic lesions, we injected mice with 150 mg/kg of D-Luciferin intra-peritoneally 5 min before imaging, and then determined luciferase activities of human ectopic lesions in mice using In Vivo Image System.

Endometriosis Treatment with C-DIM: Endometriosis was induced to mice with auto- and hetero-transplantation method as described above. After ectopic lesions were established in mice (3rd week after endometriosis induction), we randomly divided mice with endometriosis into two groups and then interperitoneally injected mice in the experimental group 25 mg/kg of C-DIM for three weeks (once a day, daily), and injected mice in the control group with the vehicle (5% DMSO and 10% 2-hydroxypropyl-β-cyclodextrin, once a day) for three weeks. In the case of the auto-transplantation model, we isolated mouse ectopic lesions treated with C-DIM versus the vehicle from mice with endometriosis at the estrus stage in the 3rd week after drug treatment and then determined their volume. In the case of the hetero-transplantation model, we determined the luciferase activity of the human ectopic lesions treated with C-DIM versus vehicle in SCID mice with endometriosis during the drug treatment.

Immunohistochemistry: Immunostaining was performed with 10% neutral-buffered, formalin-fixed, and paraffin-embedded sections of mouse tissue, as previously described. For immunostaining, sections were dewaxed, rehydrated, and boiled for 10 min in 10 mM citrate buffer, pH 6.0. To reduce nonspecific binding of antibodies, sections were washed in phosphate-buffered saline with 0.1% Tween-20 (PBST) again and preincubated with 10% Goat Serum in PBST for 1 h at room temperature. We determined Nr4a1 levels in the uterus, eutopic endometrium, and ectopic lesions with antibodies against Nr4a1(NB100-5674, Novus, 1:300). The specific antigens were visualized with the DAB (3,3'-Diaminobenzidine) substrate kit. The immunostaining intensity was quantified using the ImageJ program.

Statistical analysis: All of the experiments were repeated a minimum of three times. The data are expressed as the mean±standard error (SE). One-way analysis of variance was used to determine statistical significance. P values<0.05 were considered statistically significant.

Example 2: Expression of NR4A1 and Effects of Receptor Knockdown

Figure 1B:
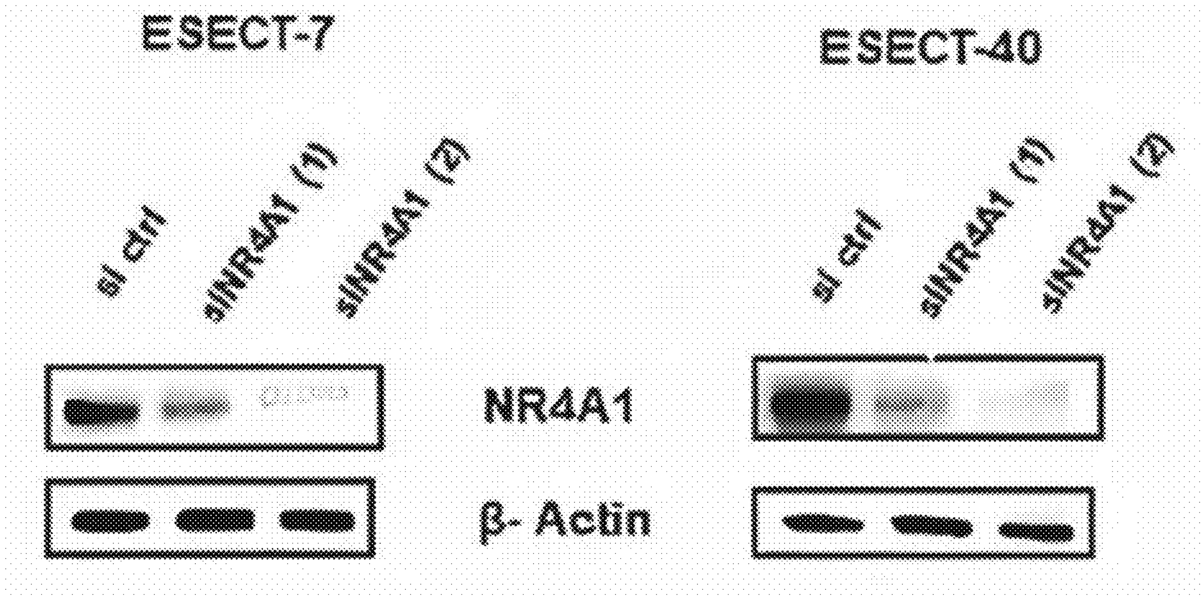
Figure 1C:
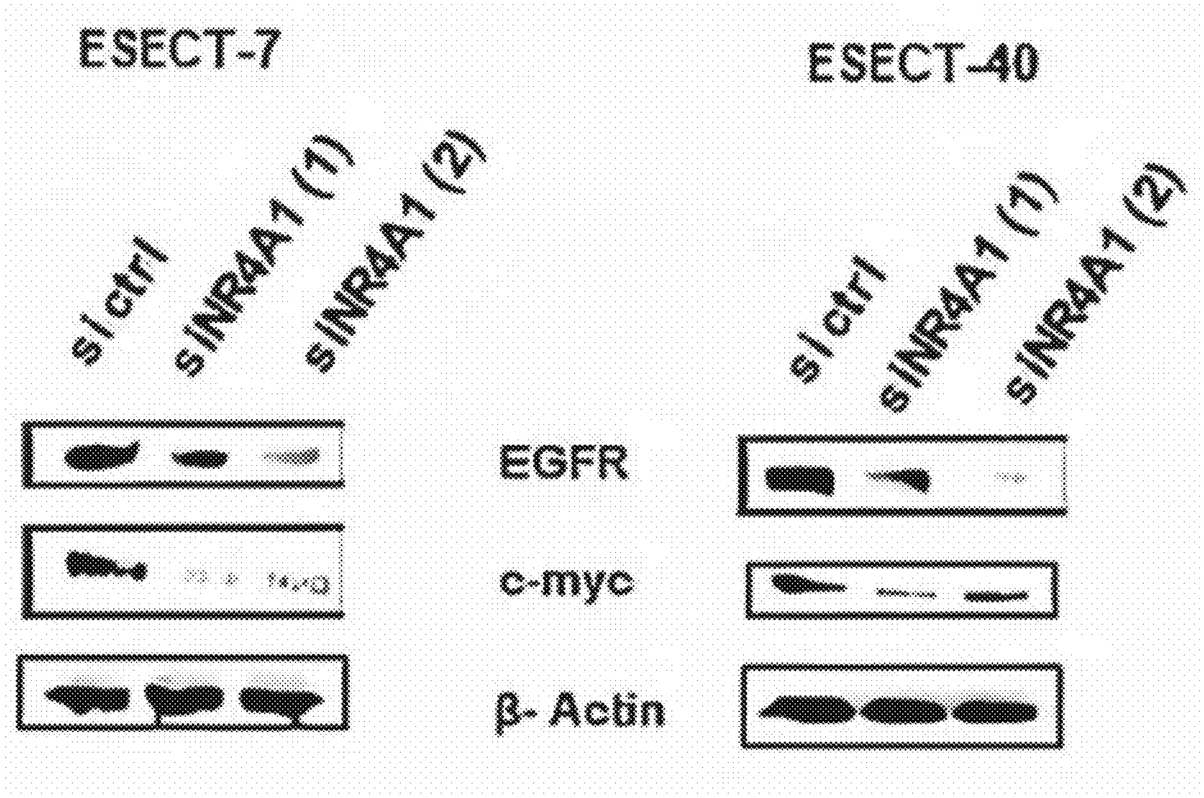
Figure 1D:
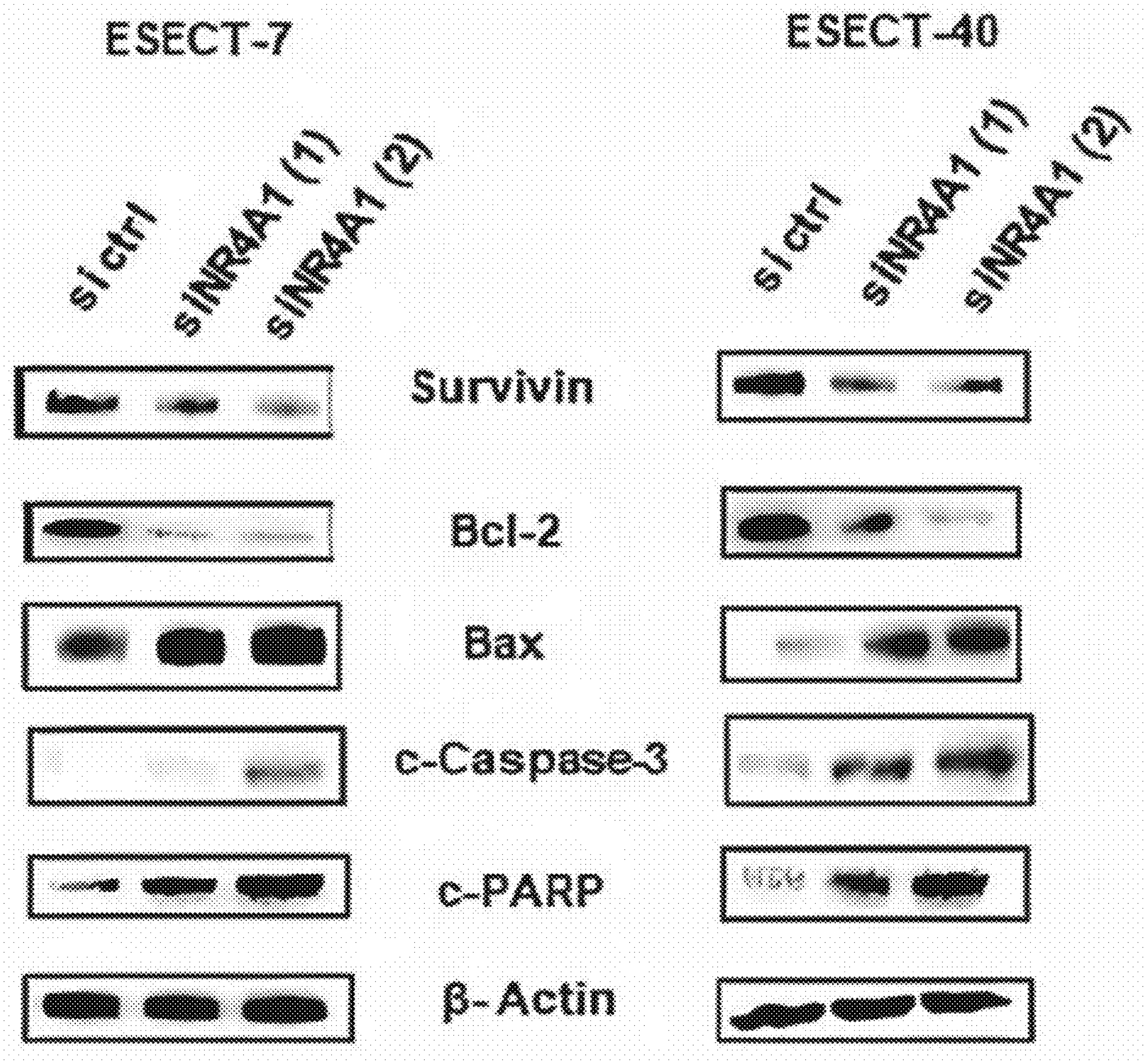
Figure 1E:
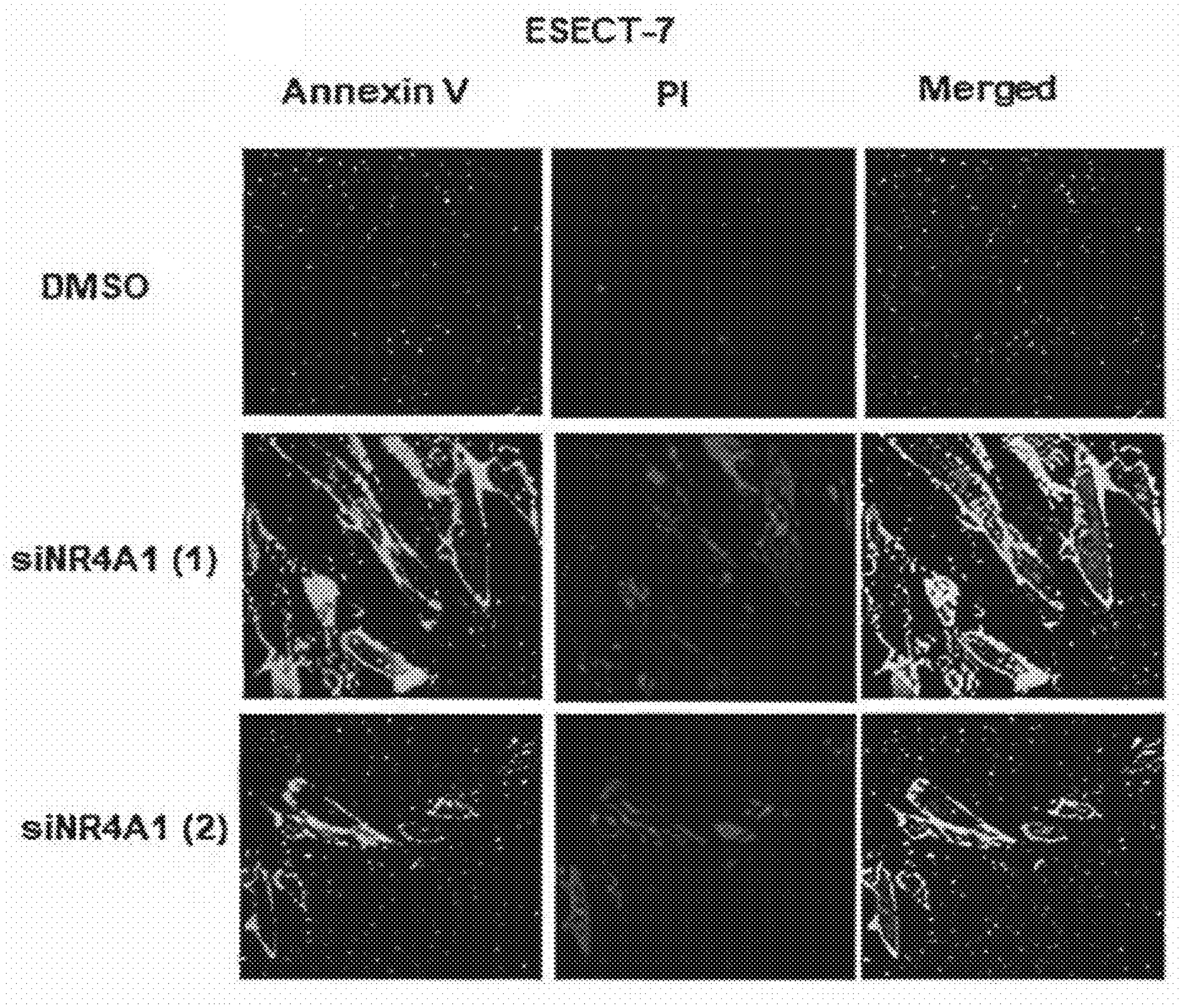
FIG. 1E illustrates the effects of NR4A1 knockdown on Annexin V Staining, in accordance with an embodiment of the disclosure.
Figure 1E:
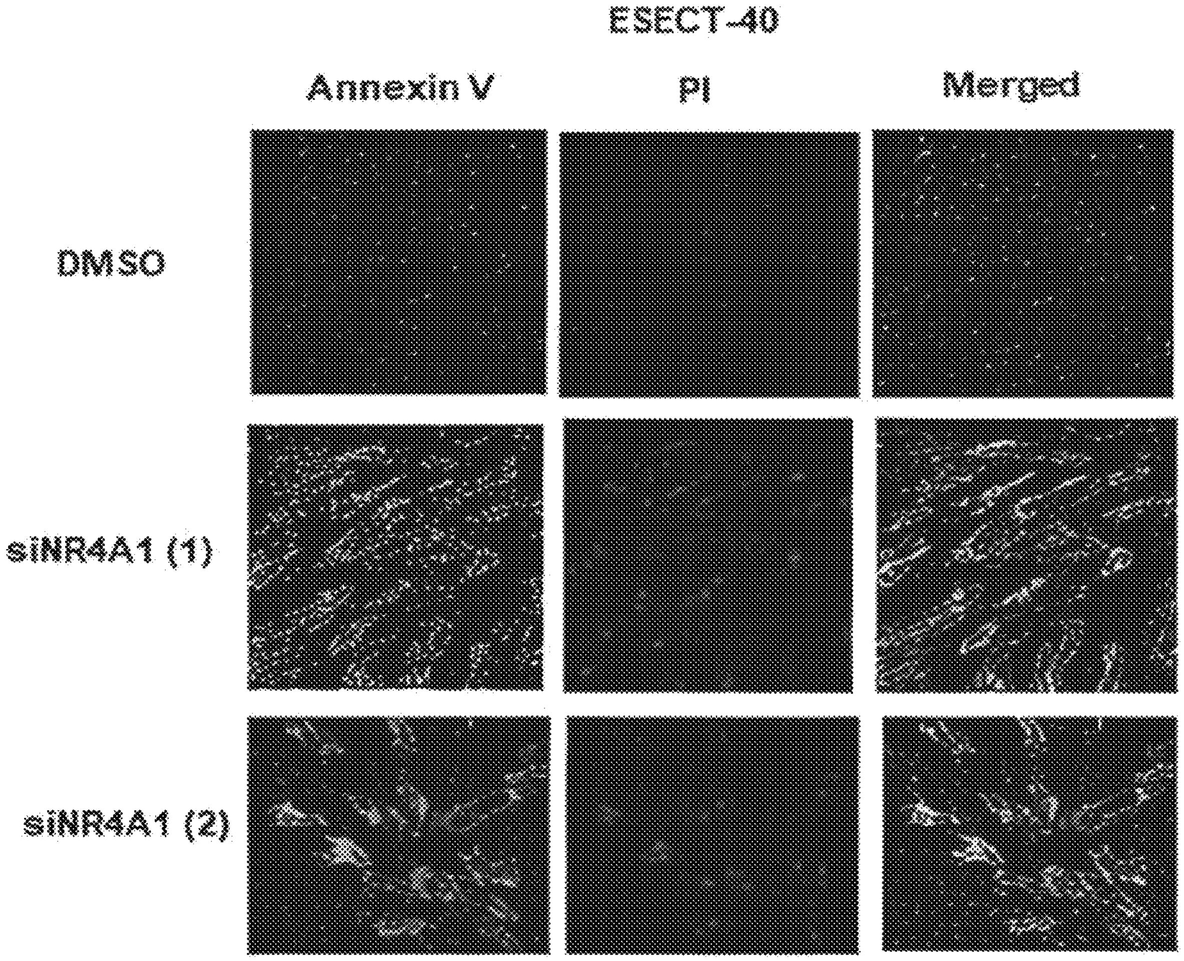

Recent studies showed that NR4A1 is expressed in endometrial cancer cells (Ishikawa and Hec1B) and played an important role in regulating cell growth, survival, migration/invasion, and related genes as previously observed in other solid tumor-derived cancer cells. Endometriotic cells also express NR4A1, and results in FIG. 1A show that knockdown of NR4A1 by RNA interference (RNAi) decreases the growth of patient-derived ESECT-7 and ESECT-40 endometriotic cells. Knockdown efficiency of both oligonucleotides was >85%, as illustrated in FIG. 1B, and loss of NR4A1 was paralleled by decreased expression of growth-promoting genes EGFR and cMyc (FIG. 1C). We also observed that knockdown of NR4A1 in endometriotic cells decreased expression of pro-survival survivin and Bcl-2 gene products, and induced Bax, Caspase-3, and PARP cleavages which are all markers of apoptosis (FIG. 1D). In addition, NR4A1 knockdown also induced Annexin V staining in ESECT-7 and ESECT-40 cells (FIG. 1E), and these results were comparable to those previously observed in endometrial cancer cells.

Example 3: Bis-Indole Derived NR4A1 Ligands: Transactivation and Function

Figure 2A:
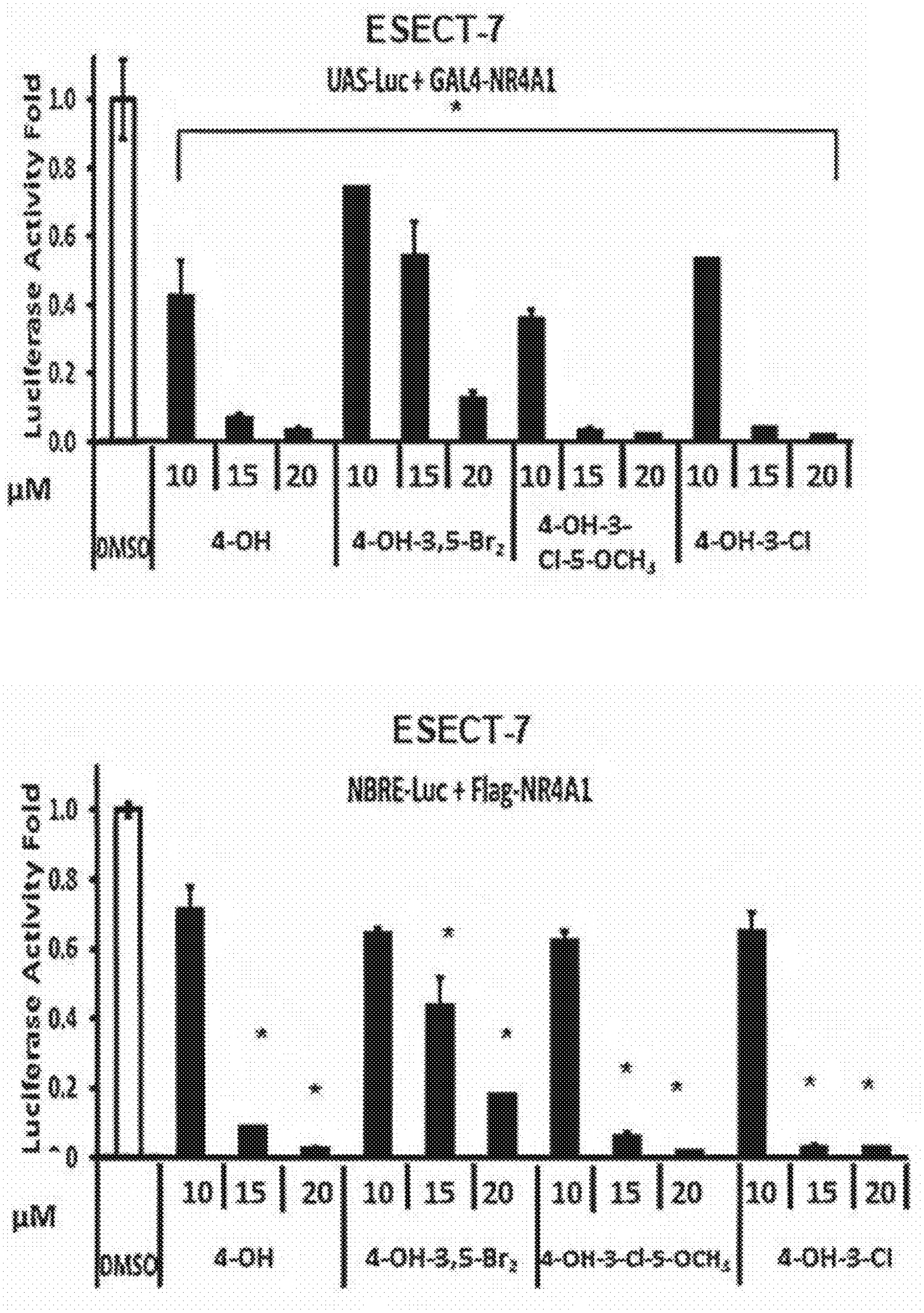
FIGS. 2A and 2B illustrate the effects of NR4A1 ligands, in accordance with embodiments of the disclosure, on transactivation and growth in endometriotic cells where ESECT-7 (2A) or ESECT-40 (2B) cells were transfected with UAS-luc/GAL4-Luc or NBRE-luc/flag-NR4A1 and treated with DIM-C-pPhOH (OH), DIM-C-pPhOH-3,5-Br2 (4-OH-3,5-Br2), DIM-C-pPhOH-3-Cl-5-OCH3 (4-OH-3-Cl-5-OCH3) or DIM-C-pPhOH-3-Cl (4-OH-3-Cl)
Figure 2B:
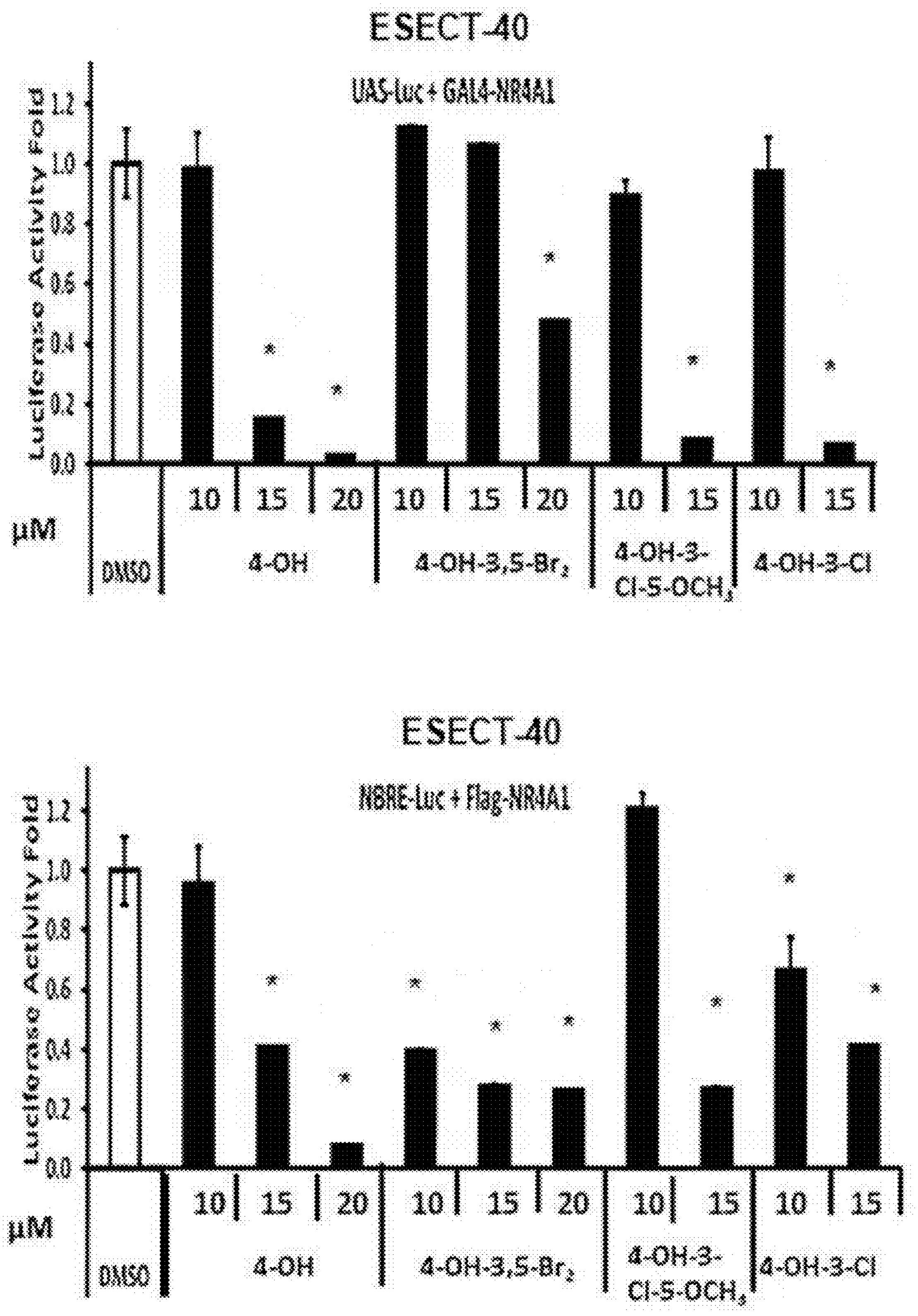
Figure 2C:
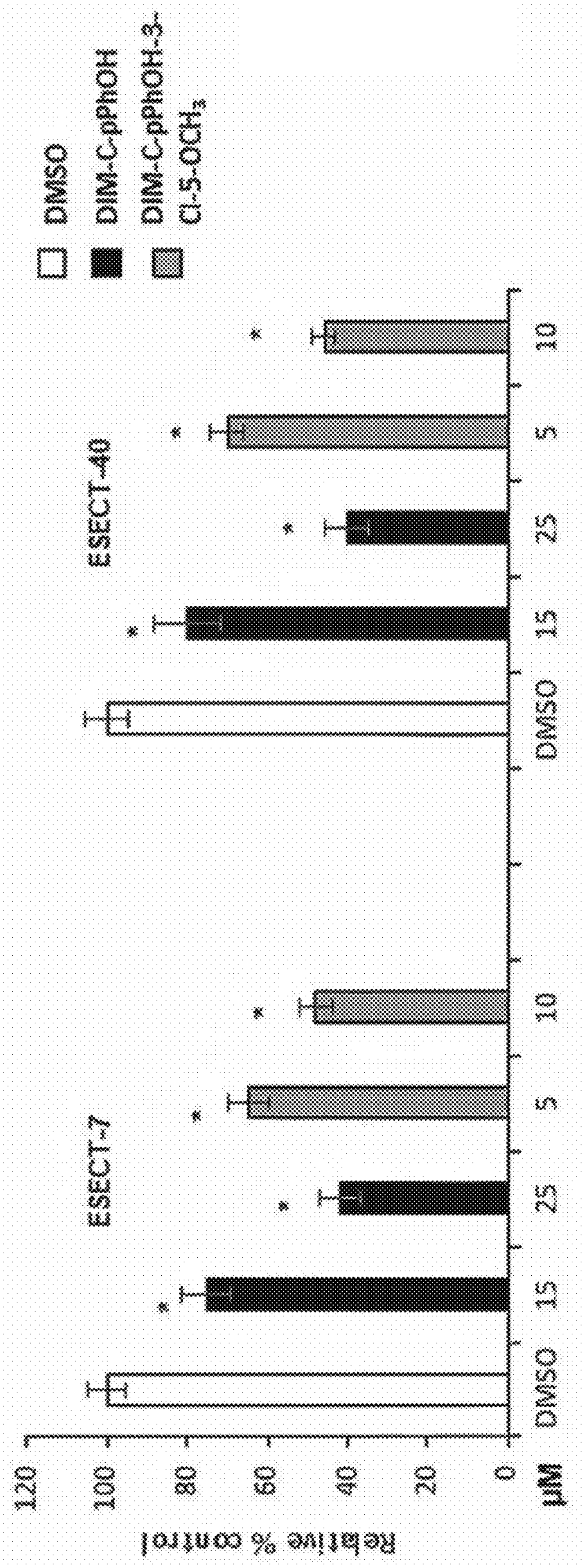
FIGS. 2C and 2D illustrate the effects of DIM-C-pPhOH and DIM-C-pPhOH-3-Cl-5-OCH3 on cell growth (2C) and growth promoting gene products (2D), in accordance with an embodiment of the disclosure.
Figure 2D:
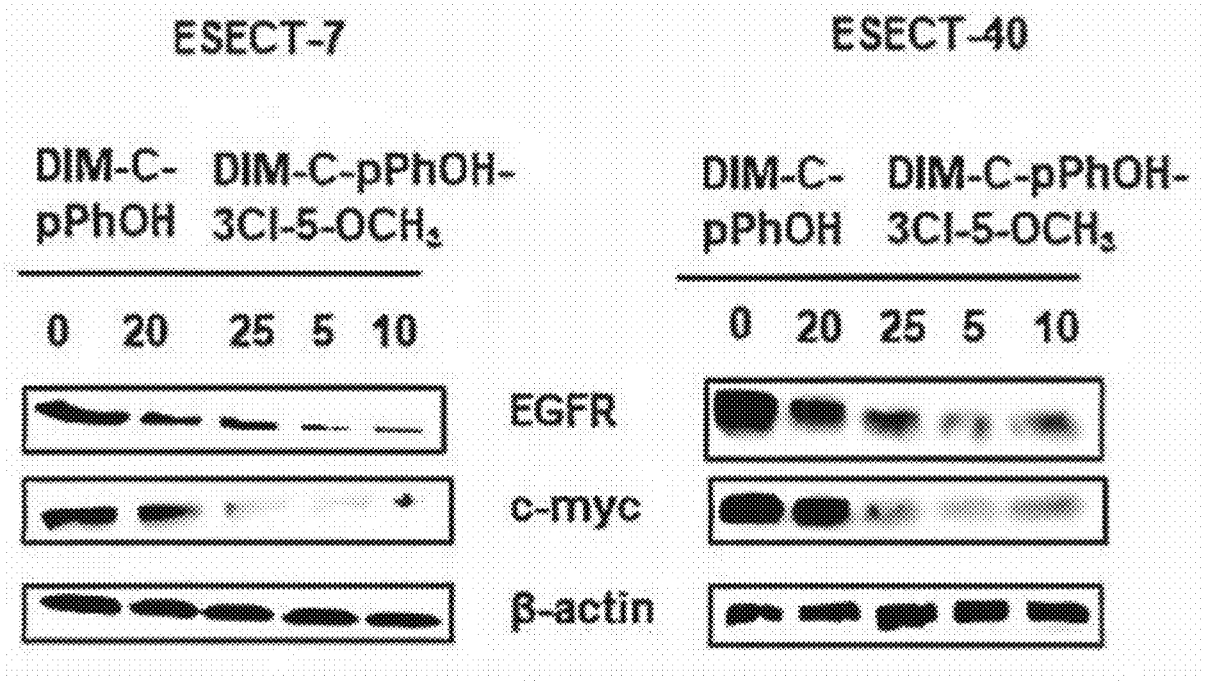
Figure 3A:
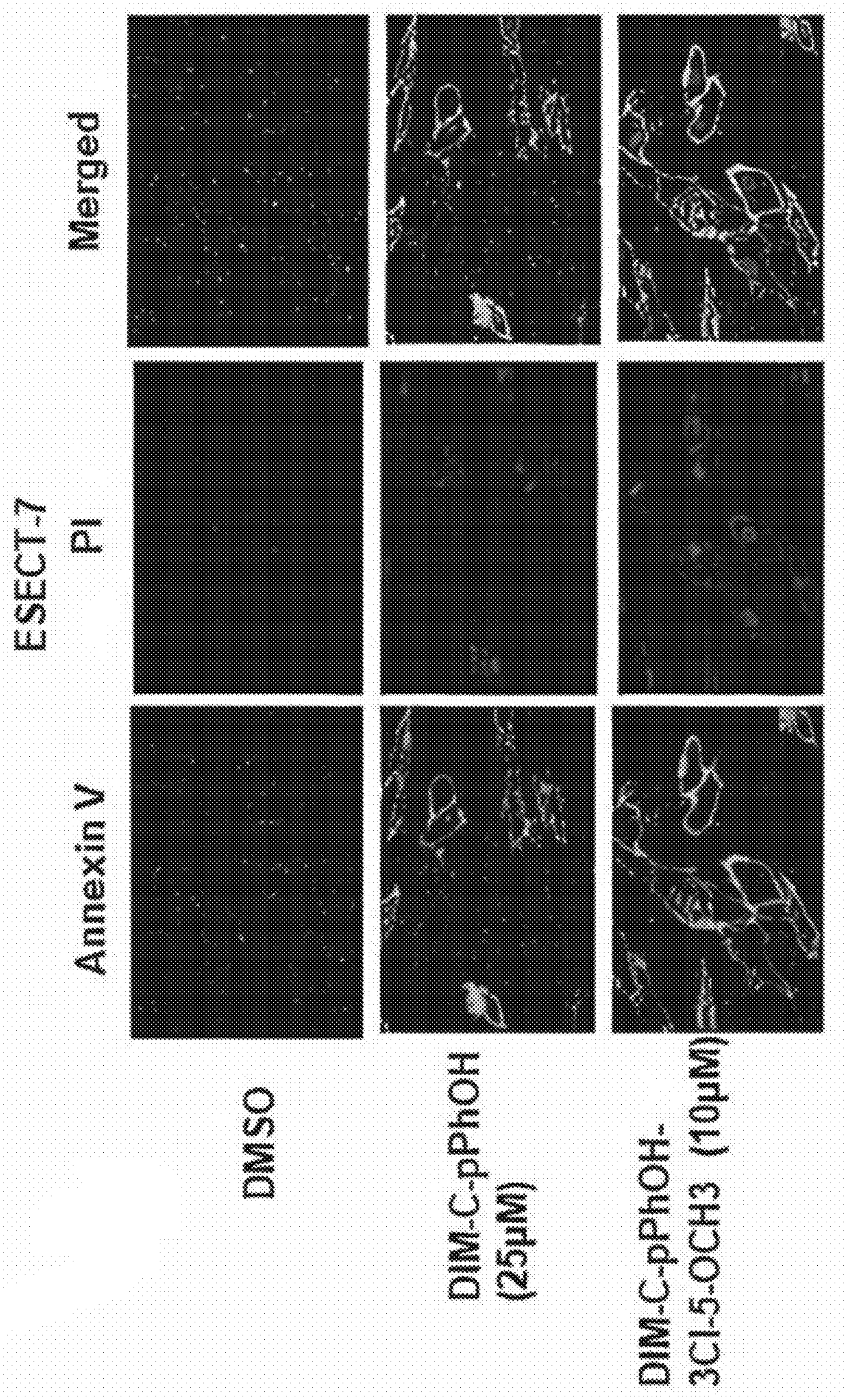
FIGS. 3A-3C illustrate how NR4A1 antagonists induce apoptosis in endometriotic cells, in accordance with an embodiment of the disclosure, where ESECT-7 (3A) and ESECT-40 (3B) cells were treated with NR4A1 antagonists and Annexin V staining was determined by fluorescence and ESECT-7 and ESECT-40 (3C) cells were treated with NR4A1 ligands for 24 hours and whole cell lysates were analyzed by western blots for proapoptotic gene products.
Figure 3A:
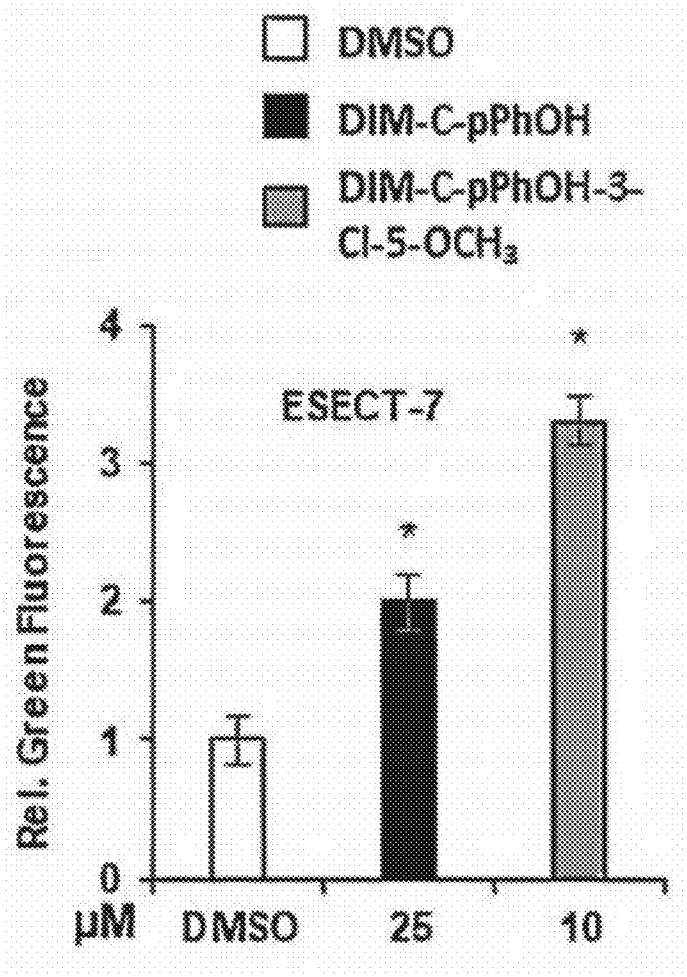
Figure 3B:
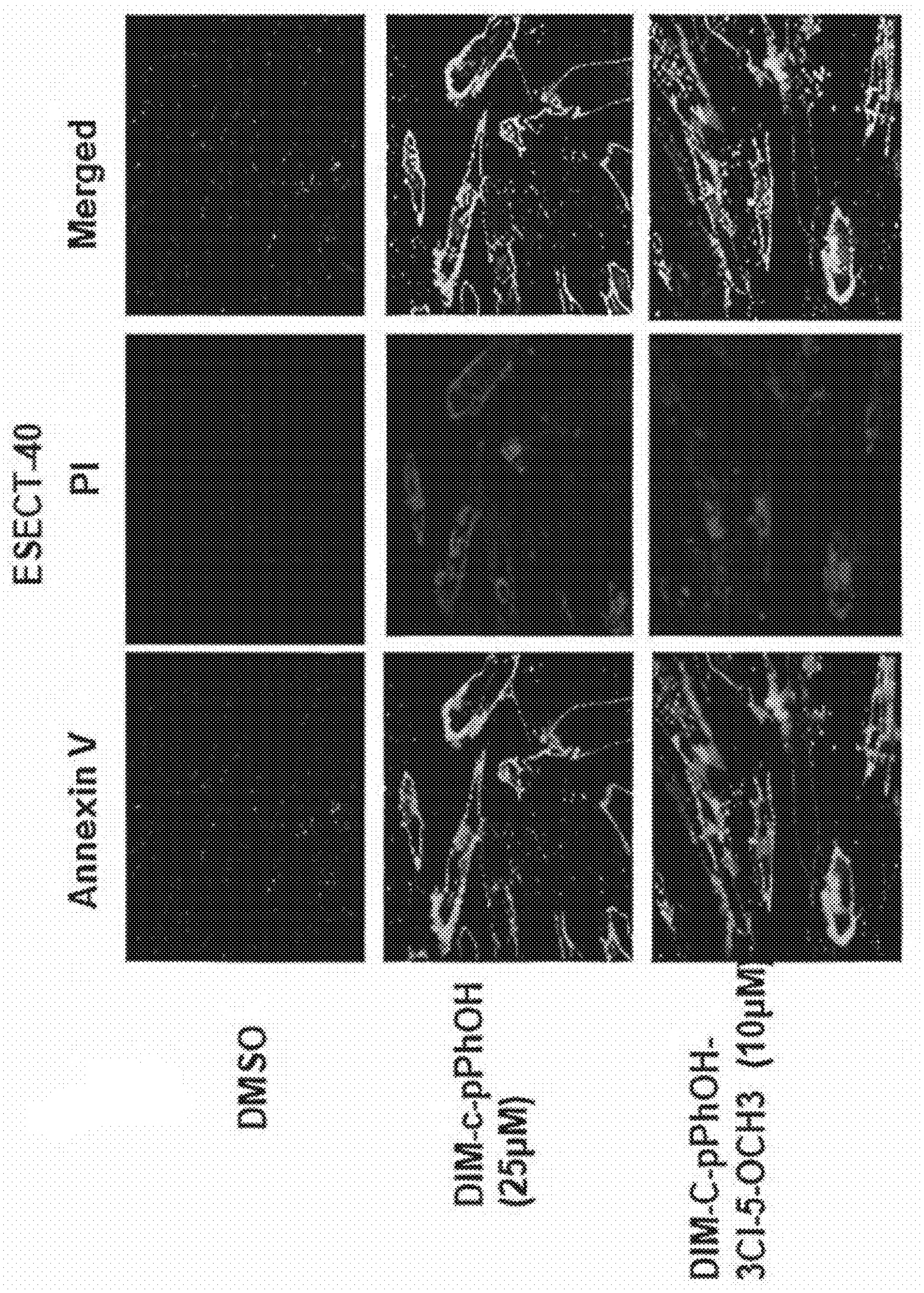
Figure 3B:
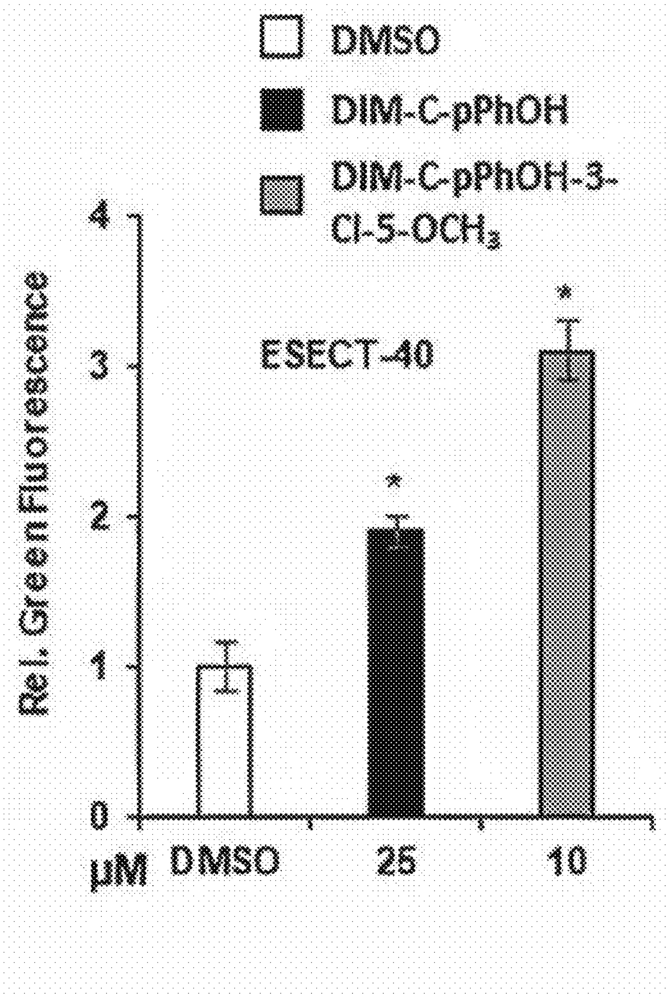
Figure 3C:
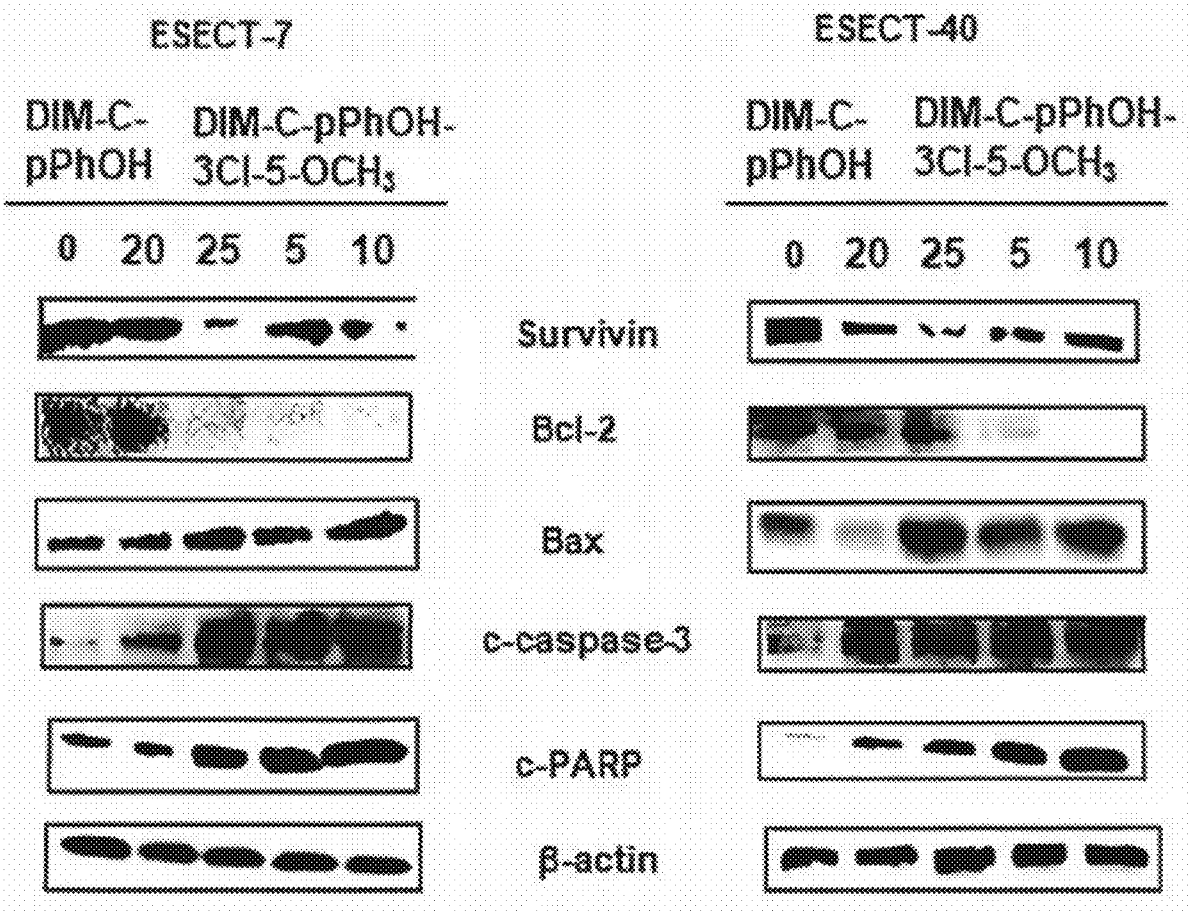

Our previous studies identified 1,1-bis(3'-indolyl)-1-(p-hydroxyphenyl)methane (DIM-D-pPhOH, CDIM8) as an NR4A1 antagonist and we have also developed several buttressed (3,5-substituted) analogs of CDIM8, to decrease the in vivo metabolism (conjugation) at the hydroxyl group and to enhance activity. Results in FIG. 2A showed that CDIM8 and the 3,5-dibromo (4-OH-3,5-Br2), 3-chloro-5-methoxy (4-OH-3-Cl-3-OCH3) and 3-chloro-(4-OH-3-Cl) buttressed analogs of DIM-C-pPhOH inhibited the intrinsic transcriptional activity of GAL4-NR4A1 and NR4A1 in ESECT-7 cells transfected with GAL4-NR4A1 chimera/Upstream Activation Sequence (UAS)-Luciferase (luc) and an NR4A1/NGFI-B response element(NBRE)-luc construct. The UAS-luc constructs contain five tandem GAL4 binding sites, and the NBRE-luc construct contains an NBRE site that binds NR4A1. The same set of compounds decreased the intrinsic transcriptional activity of NR4A1 in ESECT-40 cells (FIG. 2B). Therefore, bis-indole derived NR4A1 antagonists effectively suppressed the intrinsic transcriptional activity of NR4A1 in both human endometriotic cells and endometrial cancer cells. The comparative analysis of NR4A1 ligand derivatives revealed that DIM-C-pPhOH-3-Cl-5-OCH3 effectively suppressed the intrinsic transcriptional activity of NR4A1 as compared to other NR4A1 ligands. For example, 5-10 μM of DIM-C-pPhOH-3-Cl-5-OCH3 effectively inhibited the growth of ESECT-7 and ESECT-40 cells (FIG. 2C) and downregulated the expression of EGFR and cMyc in the same cell lines (FIG. 2D) as compared to 15-25 μM of DIM-C-pPhOH. In addition, 10 μM DIM-C-pPhOH-3-Cl-5-OCH3 significantly induced Annexin V staining in ESECT-7 (FIG. 3A) and ESECT-40 (FIG. 3B) cells as compared to 25 μM DIM-C-pPhOH. Five μM DIM-C-pPhOH-3-Cl-5-OCH3 treatment also significantly induced several markers of apoptosis including downregulation of survivin and Bcl-2 and induced Bax and cleaved PARP and caspase-3 in ESECT-7 and ESECT-40 (FIG. 3C) cells compared to 25 μM DIM-C-pPhOH.

Figure 4A:
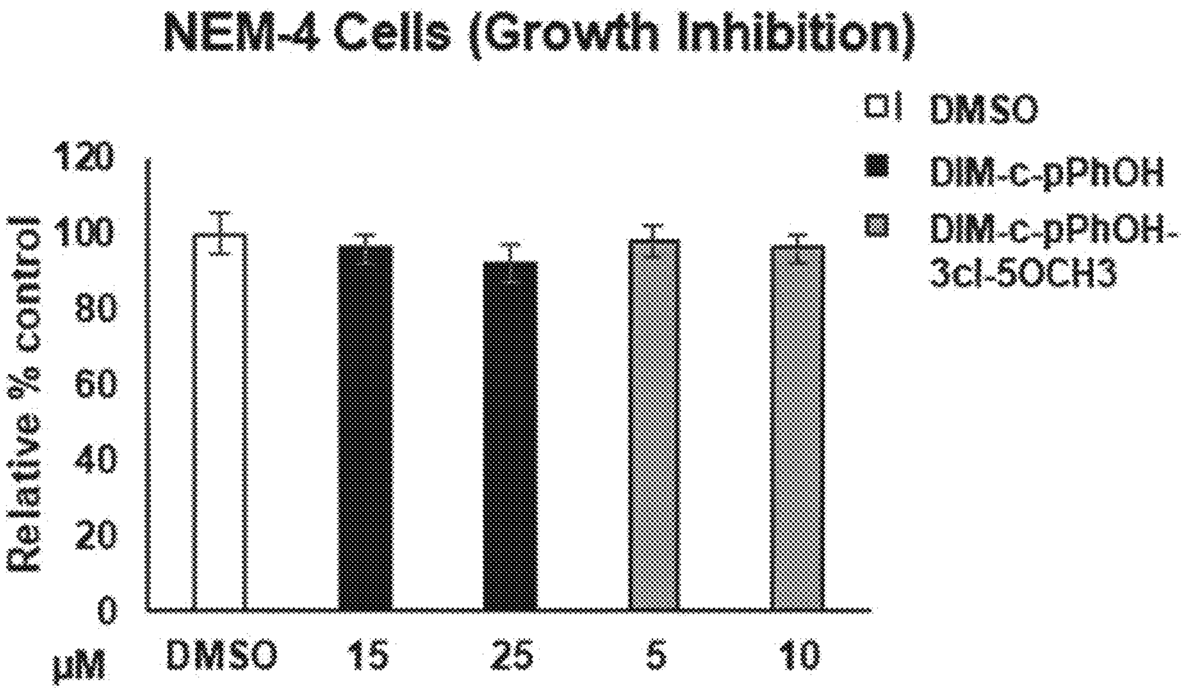
FIGS. 4A-4D illustrate the effects of NR4A1 ligand on normal endometrium (NEM) cells, in accordance with an embodiment of the disclosure, where NEM cells were treated with NR4A1 ligands for 24 hours and effects on cell growth (4A), growth promoting gene (4B), Annexin V staining (4C) and proapoptotic gene products (4D)
Figure 4B:
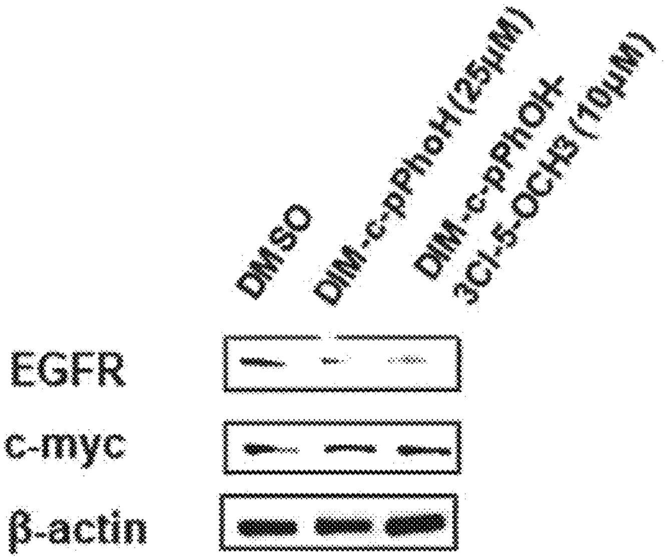
Figure 4C:
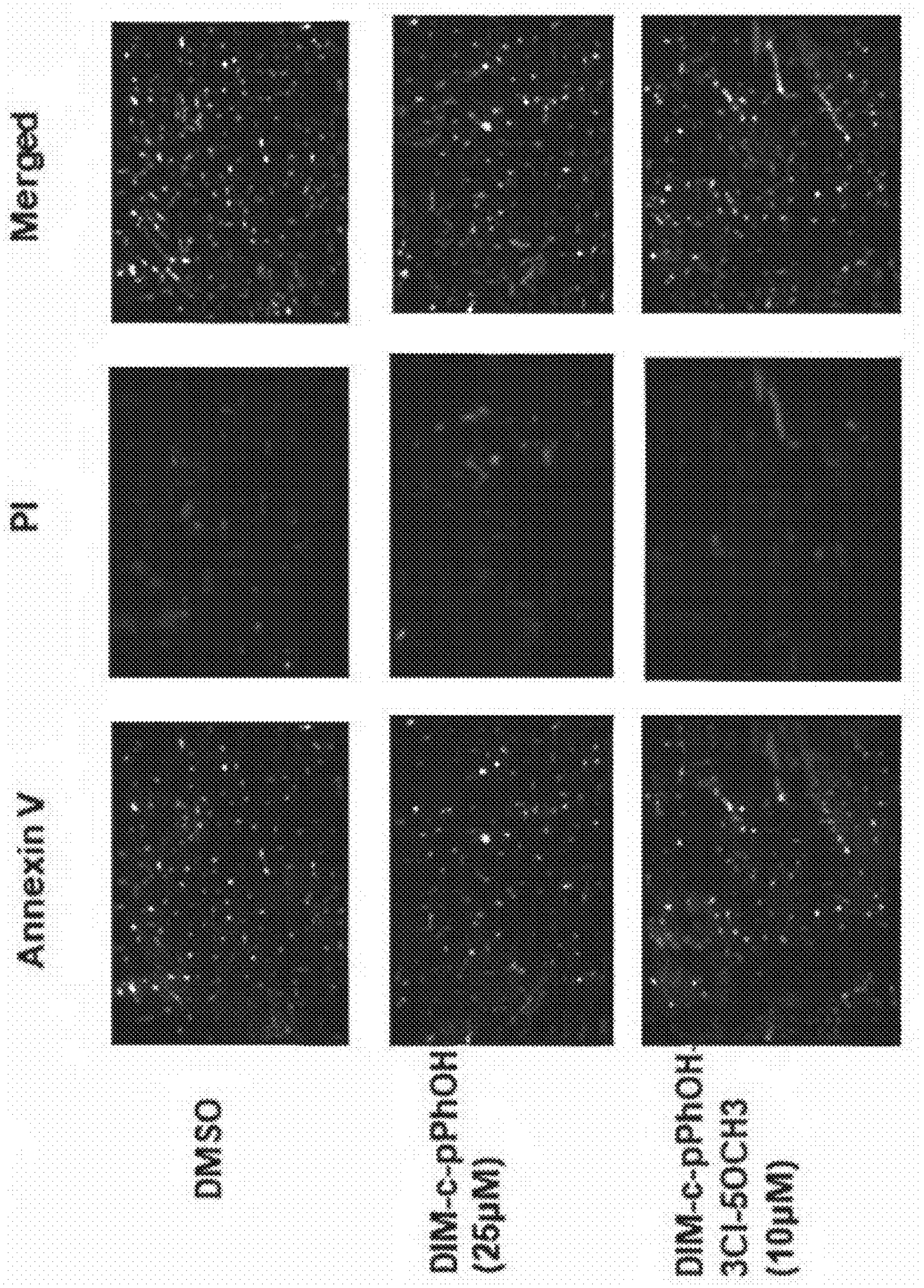
Figure 4C:
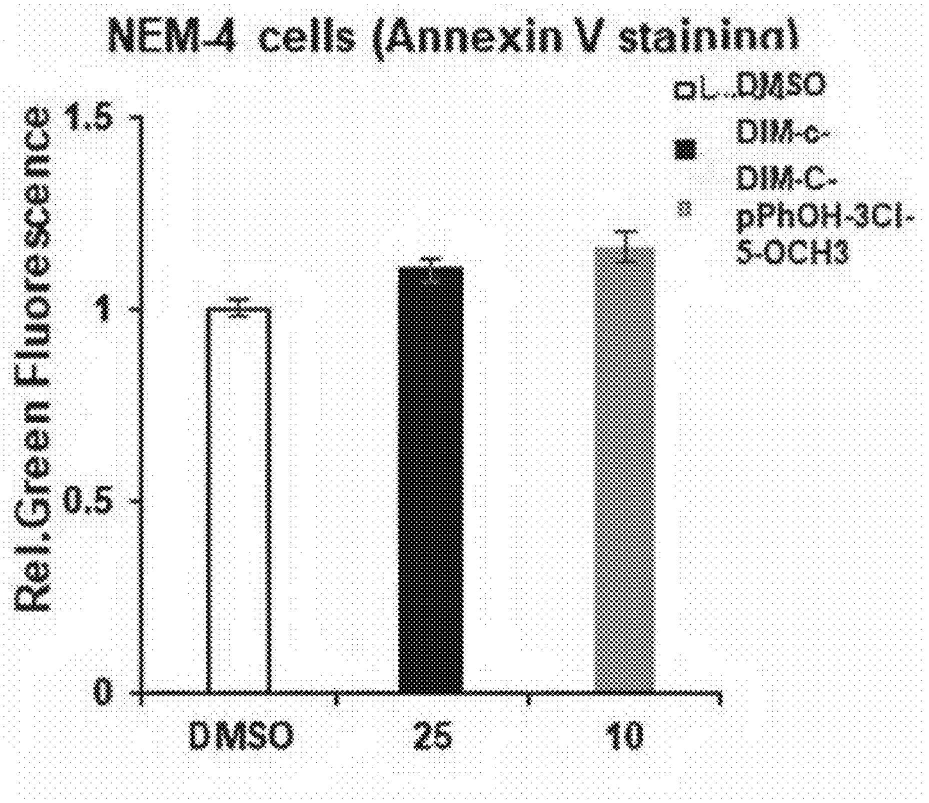
Figure 4D:
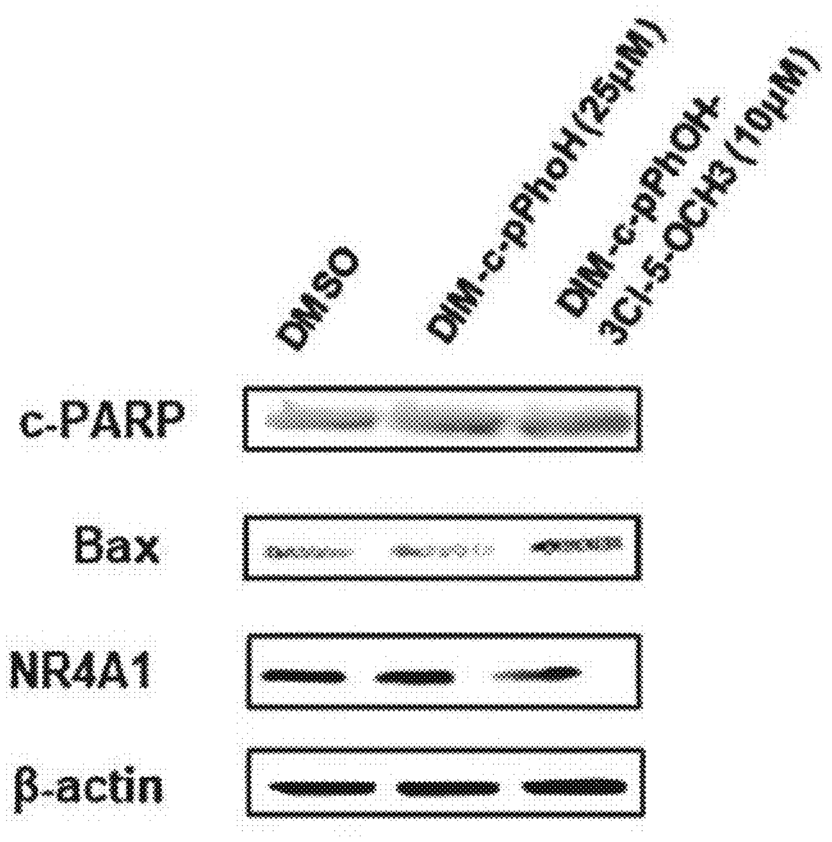

In contrast with human endometriotic stromal cells (ESECT), however, 15-25 μM DIM-C-pPhOH and 5-10 μM DIM-C-pPhOH-3-Cl-5-OCH3 treatment did not suppress the growth of normal endometrial NEM cells (FIG. 4A) and did not decrease cMyc and EGFR expression (FIG. 4B) as compared to the DMSO control. Also, 25 μM DIM-C-pPhOH and 10 μM DIM-C-pPhOH-3-Cl-5-OCH3 treatment also did not enhance Annexin V staining (FIG. 4C), levels of the cleaved form of PARP and Bax in NEM cells as compared to the DMSO control (FIG. 4D). The NEM cells also expressed NR4A1, however, the NR4A1 antagonists exhibited cell context-dependent effects and did not affect these cells and this cell-dependent specificity is typically observed for selective receptor modulators which depend not only on the receptor but also expression of specific cofactors which can differ between cell lines.

Figure 5A:
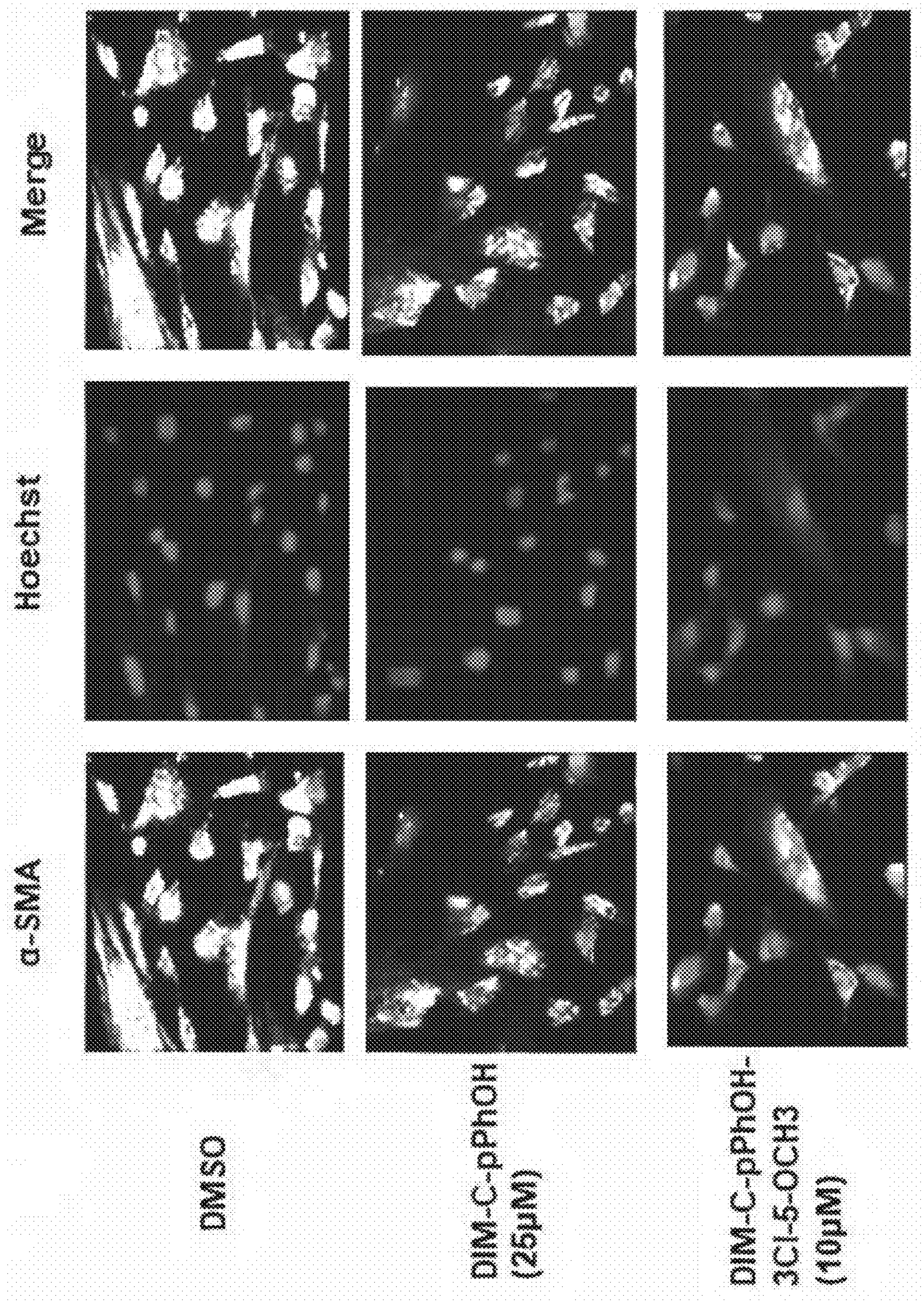
FIGS. 5A and 5B illustrate the role of NR4A1 on endometriotic cell fibrosis where ESECT-7 cells were treated with NR4A1 antagonists (5A) or transfected with siNR4A1 (1) or siNR4A1 (2) (5B), in accordance with an embodiment of the disclosure.
Figure 5B:
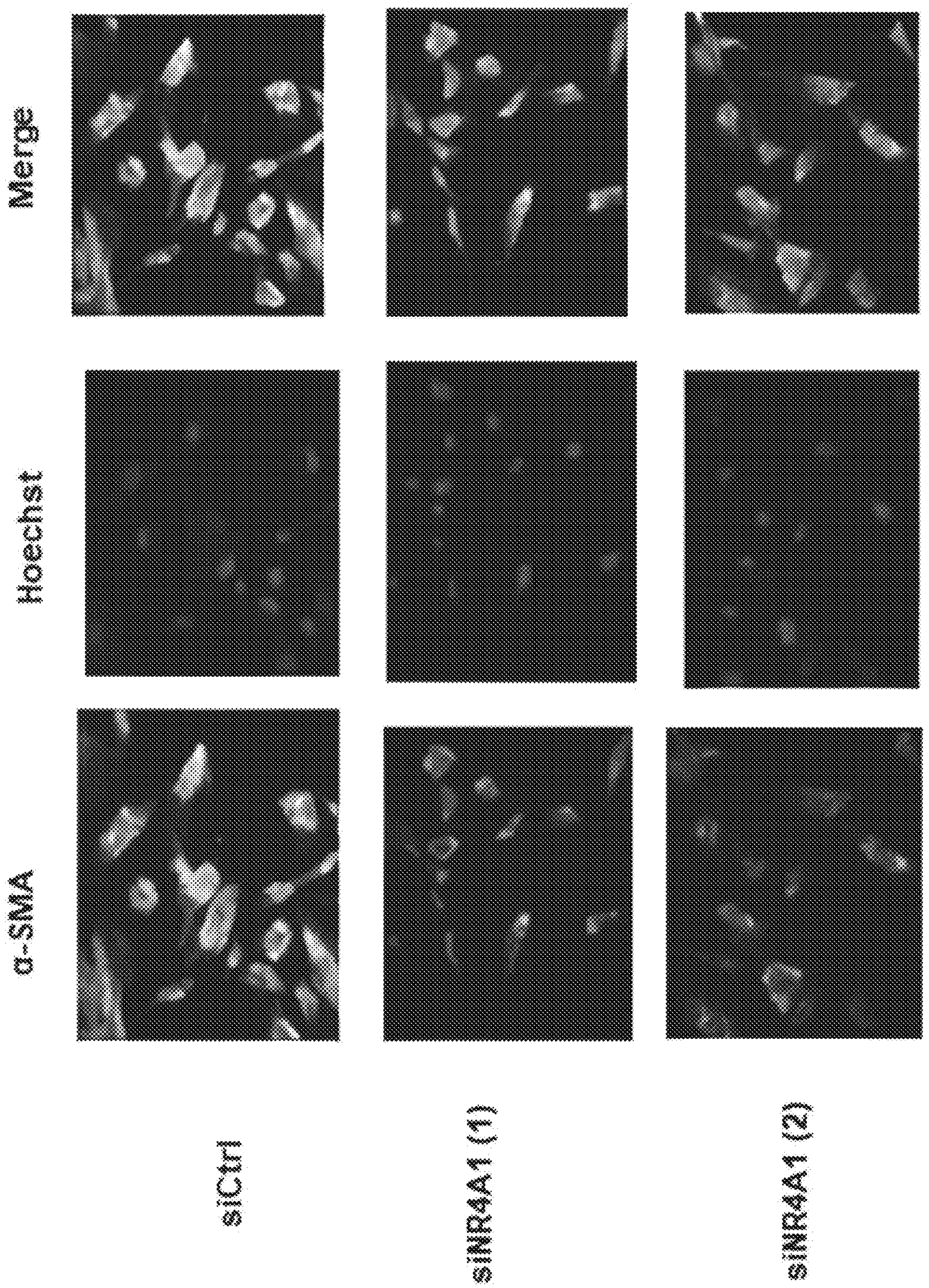
Figure 5C:
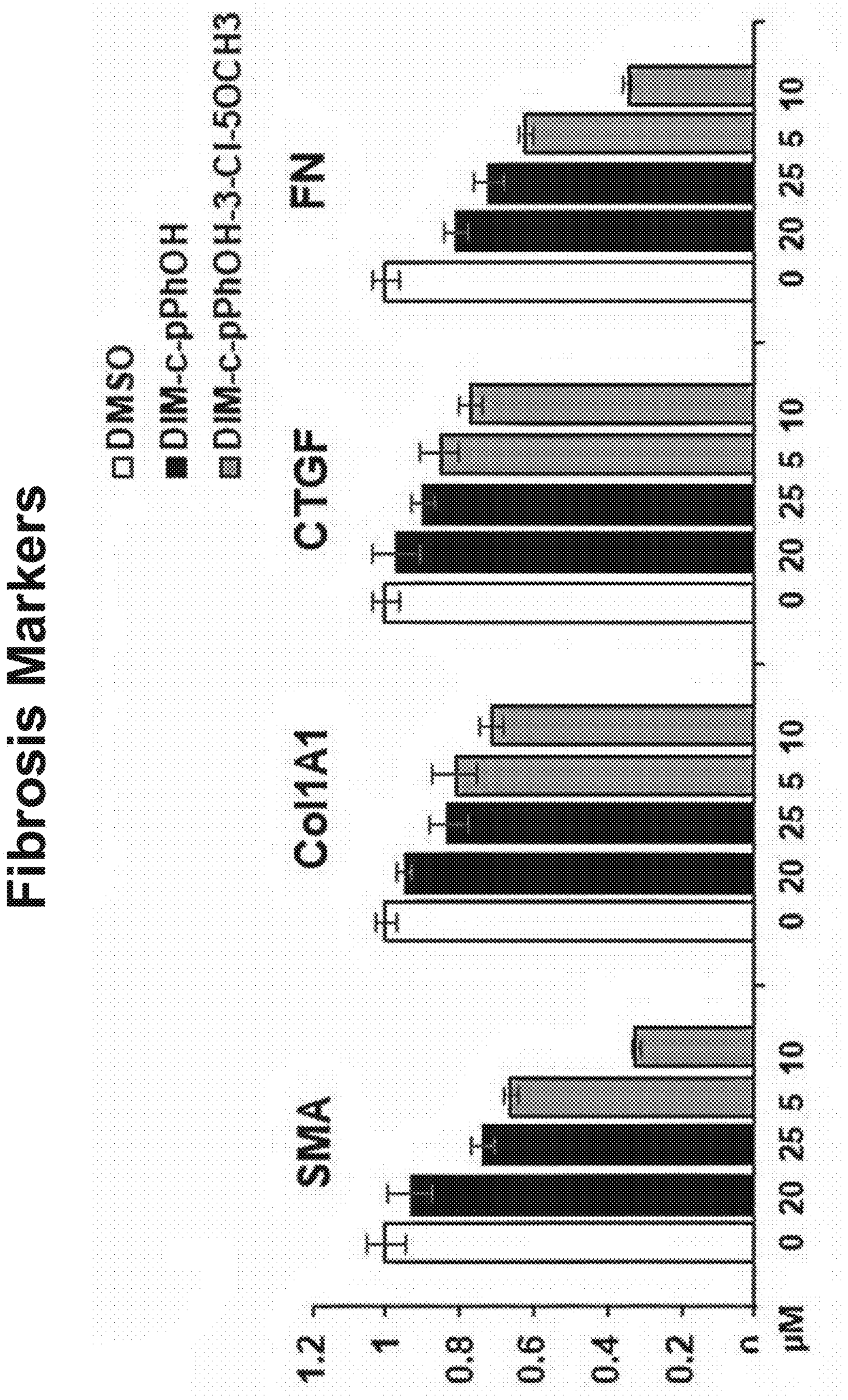
FIG. 5C graphically illustrates the effects on gene expression of fibrosis markers for ESECT-7 cells treated with NR4A1 ligands for 24 hours, in accordance with an embodiment of the disclosure.

Previous studies in stromal-derived endometriotic cells showed that knockdown of NR4A1 enhanced TGFβ1-induced fibrotic gene expression in human ectopic endometrial stromal cells (EESCs) and normal endometrial stromal cells (NESCs). To validate this observation, we inhibited the intrinsic transcriptional activity of NR4A1 (FIG. 5A) and reduced NR4A1 levels by siNR4A1 (FIG. 5B) in ESECT-7 endometriotic stromal cells and then determined the progression of fibrosis. The suppression of NR4A1 decreased expression of SMA levels in ESECT-7 cells as compared with their control (FIGS. 5A and 5B). In addition to SMA, 20-25 μM DIM-C-pPhOH and 5-10 μM DIM-C-pPhOH-3-Cl-5-OCH3 also decreased mRNA levels of fibrosis makers (such as FN, Col1A1, and CTGF) mRNA level in ESECT-7 cells compared to the DMSO control (FIG. 5C).

Figures 6C, 6D:
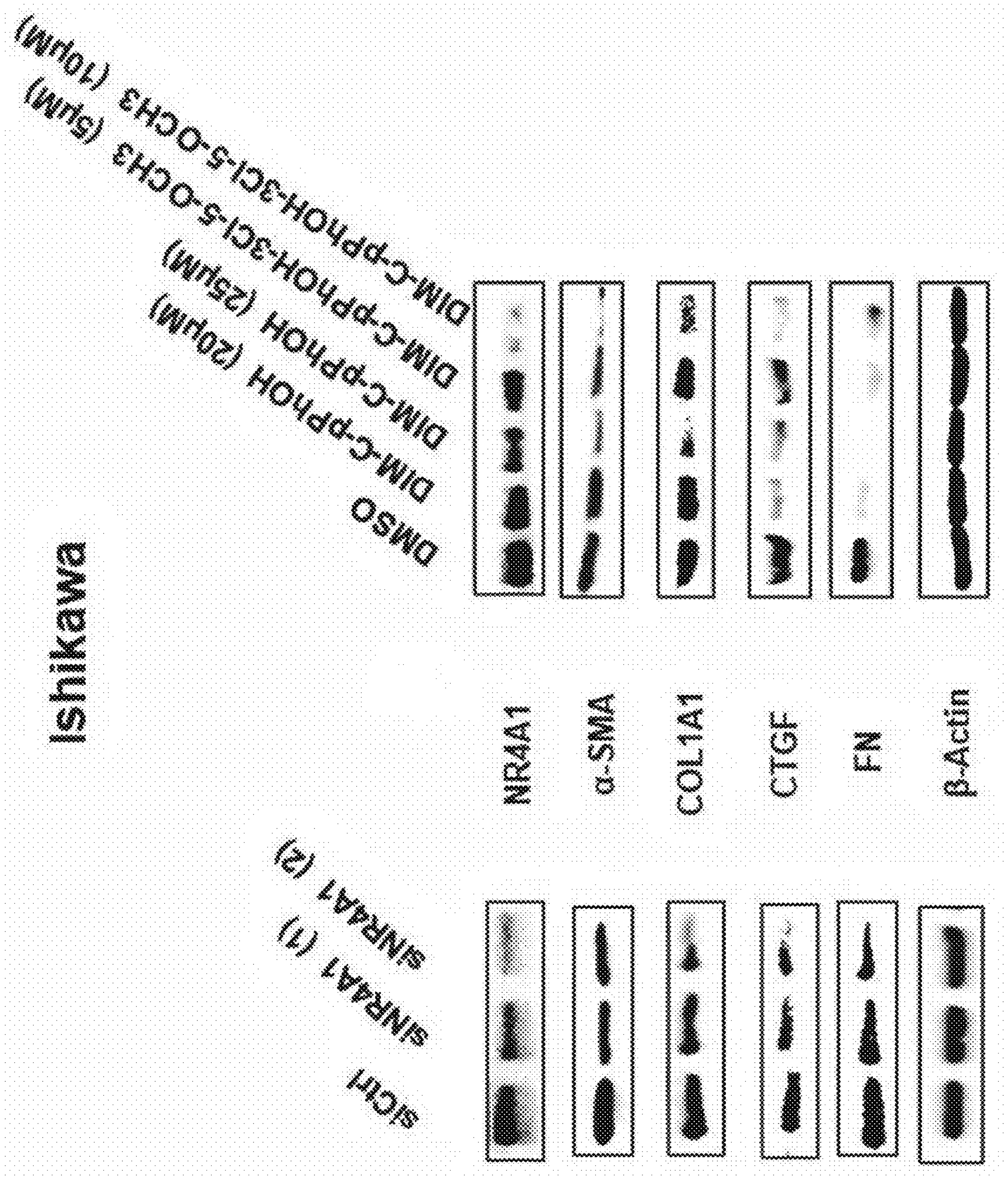
FIGS. 6C and 6D illustrate the effects of NR4A1 antagonists and receptor knockdown on Ishikawa cells transfected with siNR4A1 oligonucleotides (6C) or treated for 24 hours with NR4A1 antagonists (6D), in accordance with an embodiment of the disclosure.

Example 4: The Effect of NR4A1 Antagonist in Fibrosis of Endometriotic Cells Versus Endometrial Cancer Cells To validate NR4A1 function in fibrosis progression of human endometrial cells, we employed immortalized human endometrial epithelial cells (IHEECs) as normal human endometrial epithelial cells because IHEECs were not transformed in SCID mice (https://www.ncbi.nlm.nih.gov/pmc/articles/PMC1892381/). As the control, we employed epithelial-derived Ishikawa endometrial cancer cells because the NR4A1 inhibitor prevents growth and survival of Ishikawa cells. The knockdown of NR4A1 (FIG. 6A) and DIM-C-pPhOH and DIM-C-pPhOH-3-Cl-5-OCH3 treatment (FIG. 6B) decreased expression of fibrosis markers (α-SMA, COL1A1, FN, and CTGF) in IHEECs as compared to their control. The knockdown of NR4A1 (FIG. 6C) and DIM-C-pPhOH and DIM-C-pPhOH-3-Cl-5-OCH3 (FIG. 6D) also decreased expression of fibrosis markers (α-SMA, COL1A1, FN, and CTGF) in Ishikawa cells. Therefore, the activation of NR4A1 stimulates the fibrosis progression of endometriosis, as observed in the endometrial epithelial cancer cell line.

Example 5: Expression Levels of NR4A1 were Elevated in Endometriotic Tissues as Compared with the Normal Uterus To determine whether the expression levels of NR4A1 are elevated in endometriotic tissues as compared with normal endometrium, we surgically induced endometriosis into mice with the auto-transplantation method. At the estrus stage in the 3rd week after endometriosis induction, ectopic lesions and eutopic endometrium were isolated from mice with endometriosis. As the control, we also isolated uterus at the estrus stage of female mice (10-week old) without endometriosis.

Figure 7A:
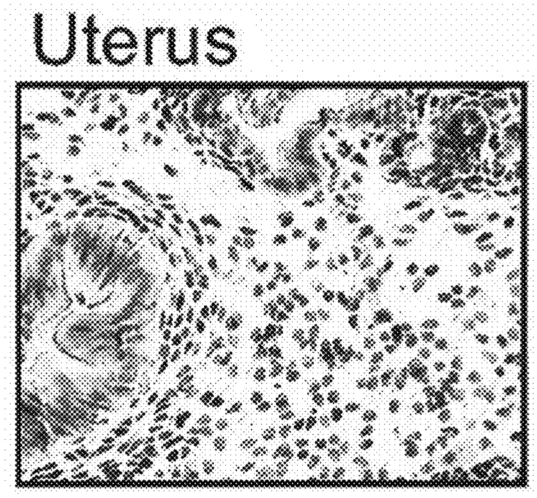
FIGS. 7A-7C illustrate Nr4a1 expression in normal mouse uterus (7A), eutopic endometrium (7B), and ectopic lesions (7C)
Figure 7B:
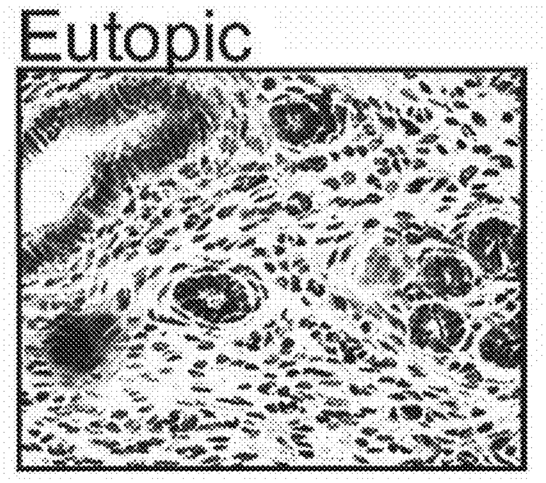
Figure 7C:
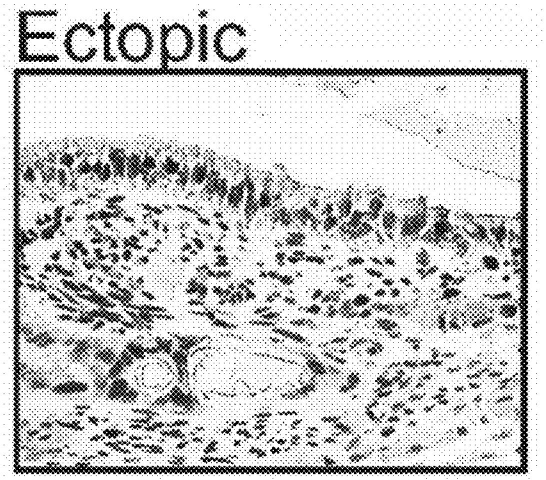
Figure 7D:
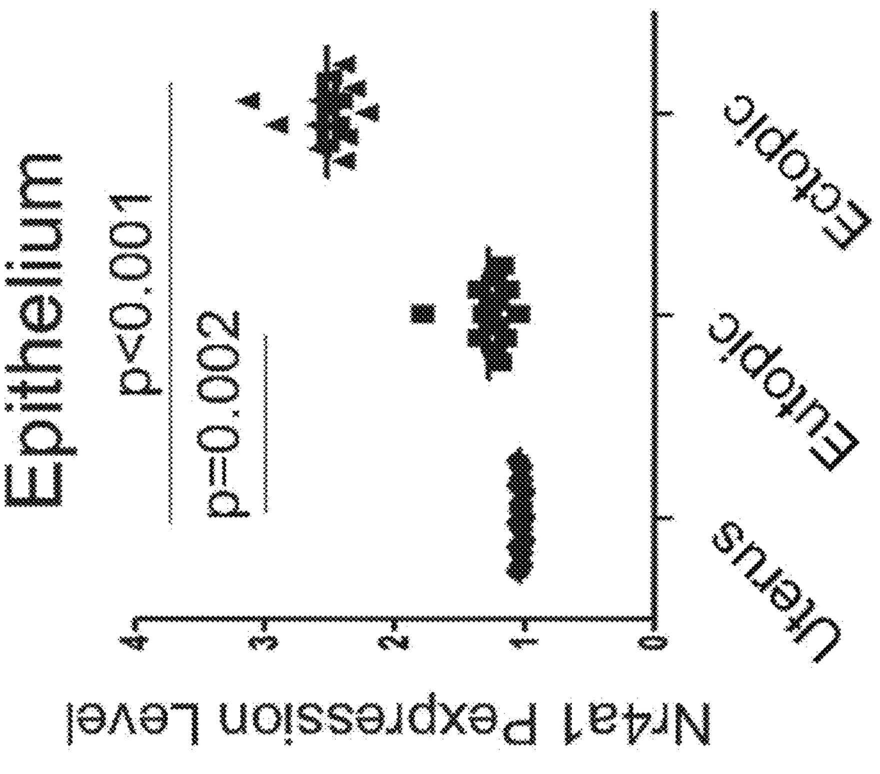
FIGS. 7D and 7E illustrate IHC signal density of Nr4a1 in the epithelium (7D) and stroma (7E) of the uterus, eutopic endometrium, and ectopic lesions.
Figure 7E:
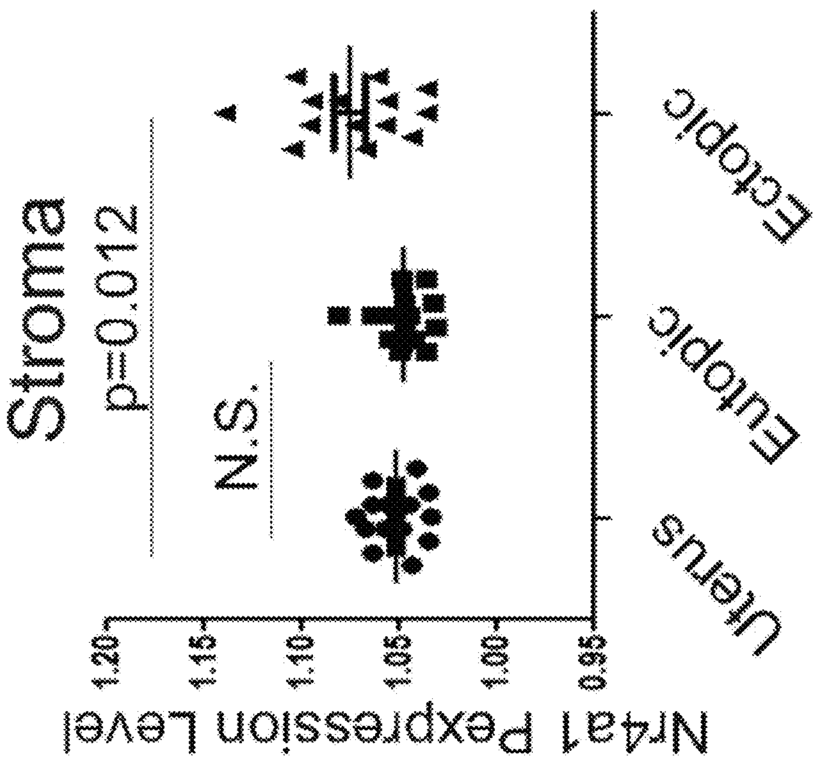

Immunohistochemistry (IHC) with the NR4A1 antibody revealed that NR4A1 levels were significantly elevated in the epithelium of ectopic lesions (2.6-fold, $p<0.001$) as compared with the epithelium of uterus (FIGS. 7A, 7C, and 7D). In addition to ectopic lesions, NR4A1 levels were also elevated in the epithelium of eutopic endometrium as compared with those in the epithelium of normal uterus (1.27-fold, $p=0.002$) (FIGS. 7A, 7B, and 7D). Therefore, epithelium of ectopic lesions and eutopic endometrium of mice with endometriosis have higher levels of NR4A1 compared to the epithelium of normal uterus. In addition to the epithelium, levels of NR4A1 in the stroma of ectopic lesions slightly elevated as compared with stroma of uterus (1.1-fold, p=0.012) (FIG. 7E). However, the level of NR4A1 was not elevated in the stroma of eutopic endometrium compared to the stroma of normal uterus (FIG. 7E). Collectively, the elevation of NR4A1 levels in endometriotic tissues was associated with endometriosis progression.

Figure 8A:
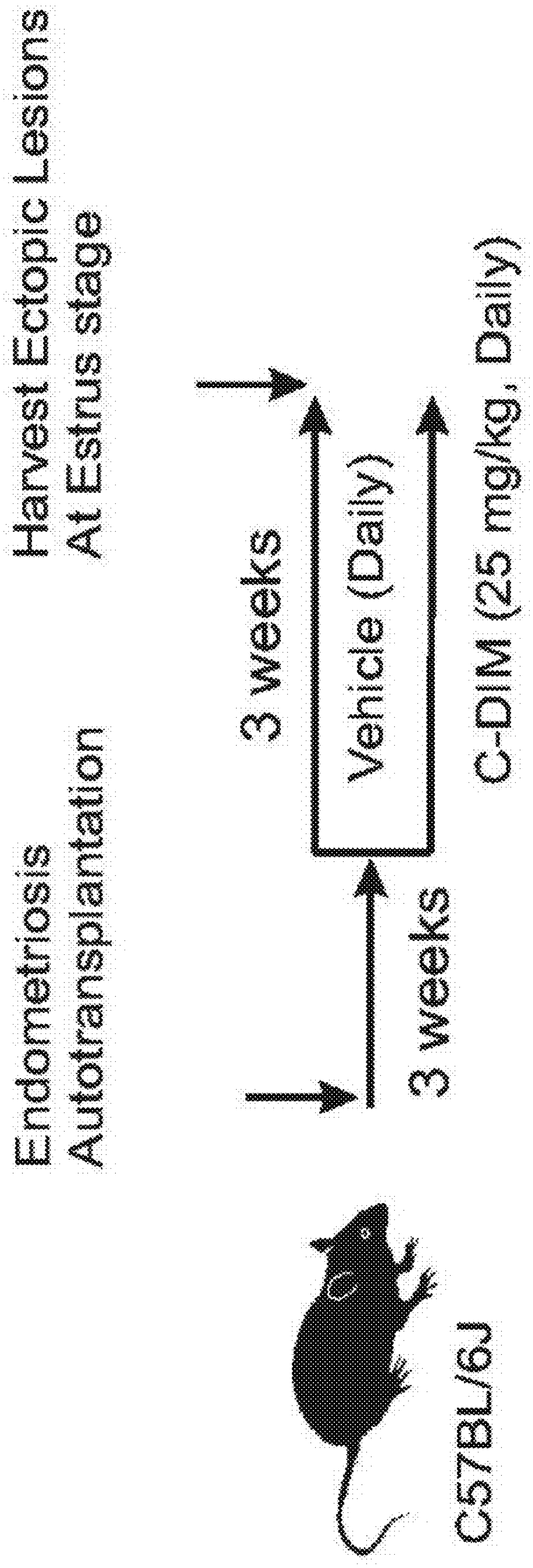
FIG. 8A schematically illustrates a method of treatment and a control method, in accordance with an embodiment of the disclosure.
Figure 8B:
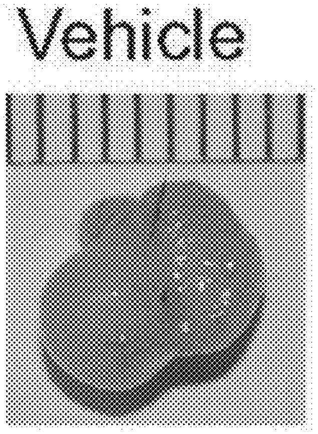
FIGS. 8B and 8C are images of ectopic lesions isolated from mice with endometriosis treated with the vehicle (B) and C-DIM (C), in accordance with an embodiment of the disclosure.
Figure 8C:
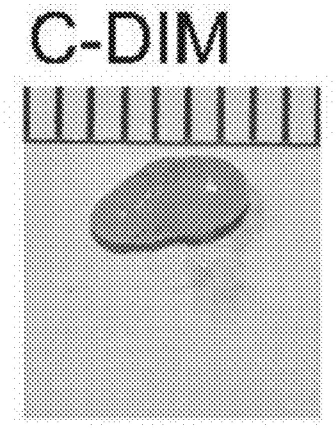
Figure 8D:
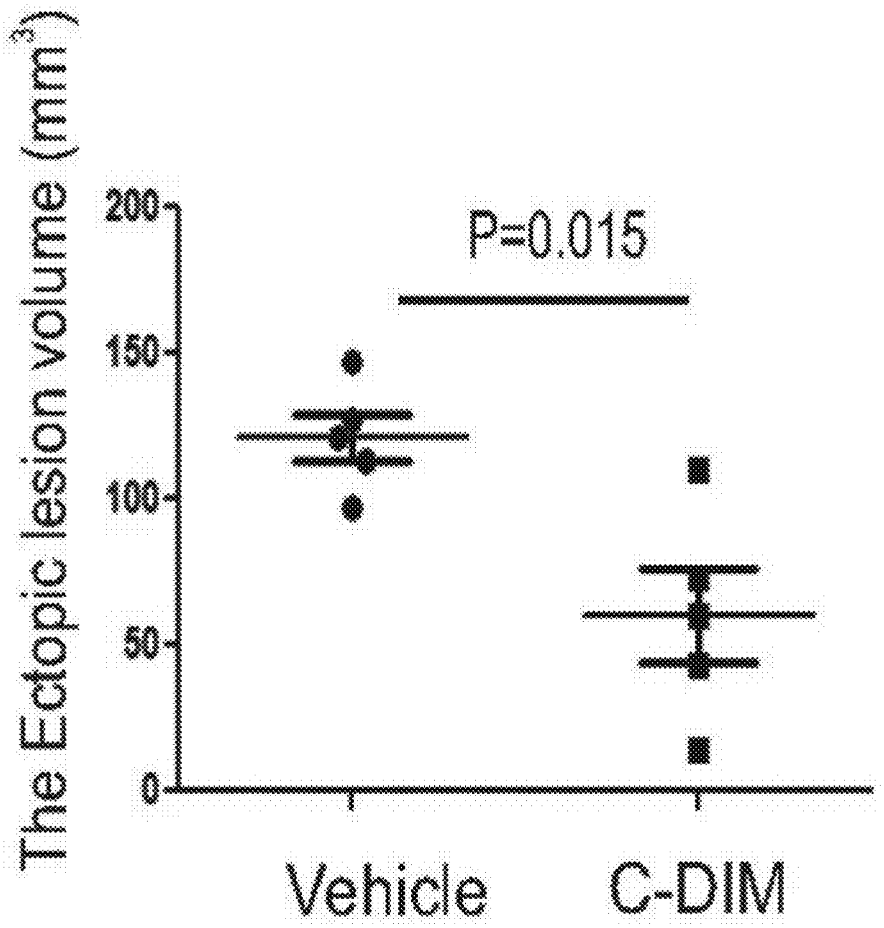
FIG. 8D graphically illustrates the volume of isolated ectopic lesions treated with the vehicle versus C-DIM, in accordance with an embodiment of the disclosure.
Figure 8E:
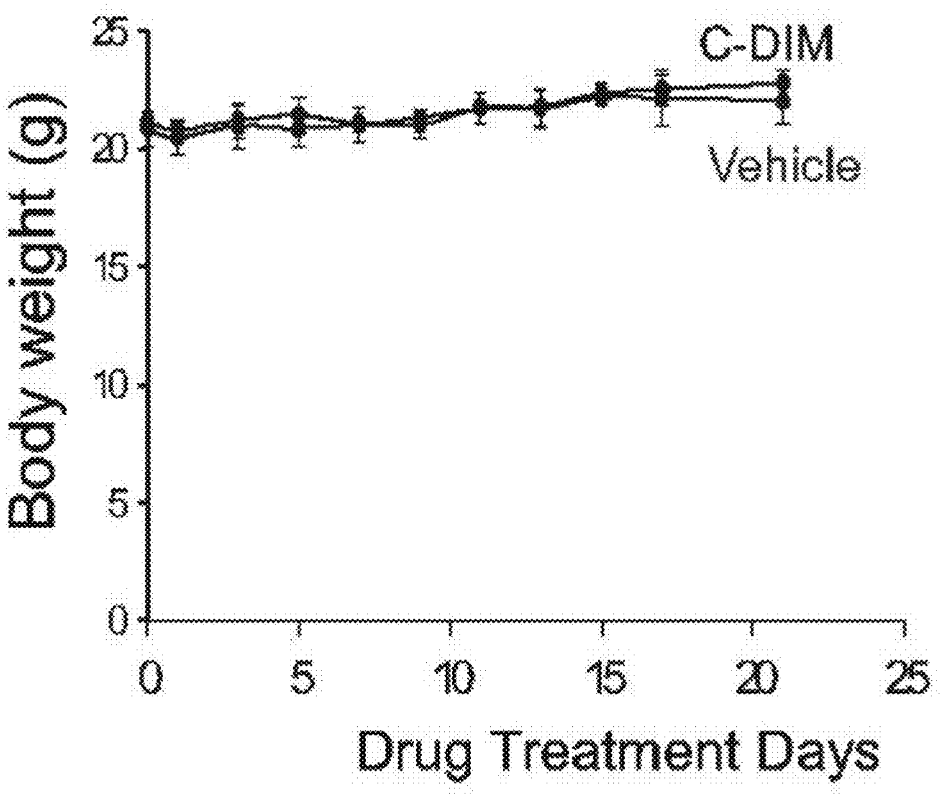
FIG. 8E graphically illustrates the bodyweight of mice treated with vehicle versus C-DIM, in accordance with an embodiment of the disclosure.

Example 6: The DIM-C-PPhOH-3-Cl-5-OCH3 Treatment Effectively Suppresses the Growth of Ectopic Lesions in Mice with Endometriosis Even though expression levels of NR4A1 were significantly elevated in ectopic lesions compared to the normal uterus, it is not clear whether the elevation of NR4A1 induces endometriosis or is simply a consequence of endometriosis. To address this question, we employed the NR4A1 specific antagonist, DIM-C-pPhOH-3-Cl-5-OCH3, to examine whether inhibition of NR4A1 in ectopic lesions suppresses endometriosis daily progression in mice with endometriosis. Based on previous our study, we treated mice with endometriosis with 25 mg/kg of DIM-C-pPhOH-3-Cl-5-OCH3 and vehicle control every day (FIG. 8A). The 25 mg/kg of DIM-C-pPhOH-3-Cl-5-OCH3 treatment significantly reduced (2.4-fold, p=0.015) the volume of ectopic lesions compared to the vehicle (FIGS. 8B, 8C, and 8D). However, DIM-C-pPhOH-3-Cl-5-OCH3 treatment did not change the bodyweight of mice as compared to the vehicle (FIG. 8E). Therefore, DIM-C-pPhOH-3-Cl-5-OCH3 treatment effectively suppressed the growth of mouse ectopic lesions in mice with endometriosis with minimal side effects.

Figure 9A:
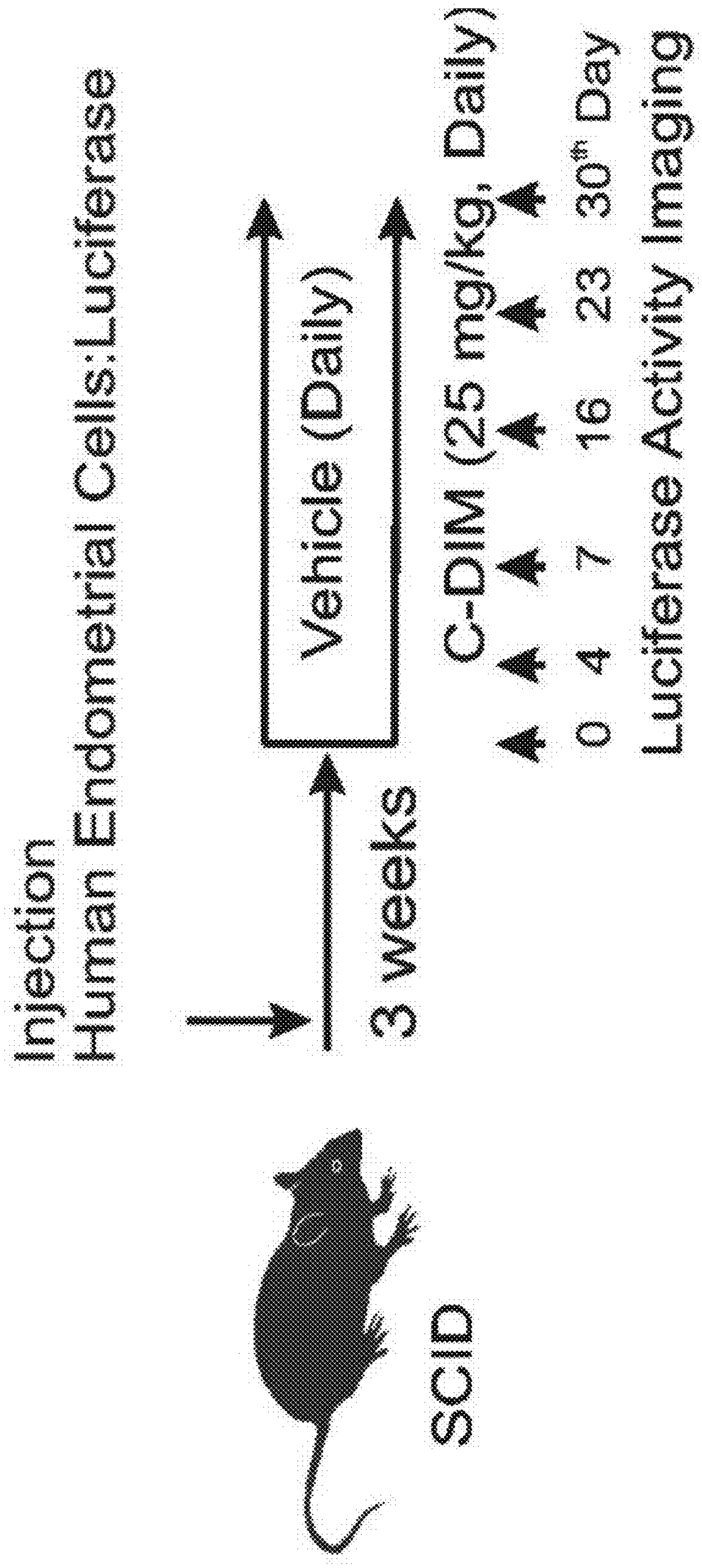
FIG. 9A schematically illustrates experiments to measure suppression of the growth of human ectopic lesions in SCID mice by DIM-C-pPhOH-3-Cl-5-OCH3 (C-DIM), in accordance with an embodiment of the disclosure, where human ectopic lesions were generated by injection of human endometrial cells expressing luciferase into SCID mice and at 3rd week after endometriosis induction, mice were randomly divided into two groups and mice in one group were treated with 25 mg/kg of C-DIM (once a day), in accordance with an embodiment of the disclosure, and mice in the other group were treated with the vehicle (once a day) for 30 days.
Figure 9B:
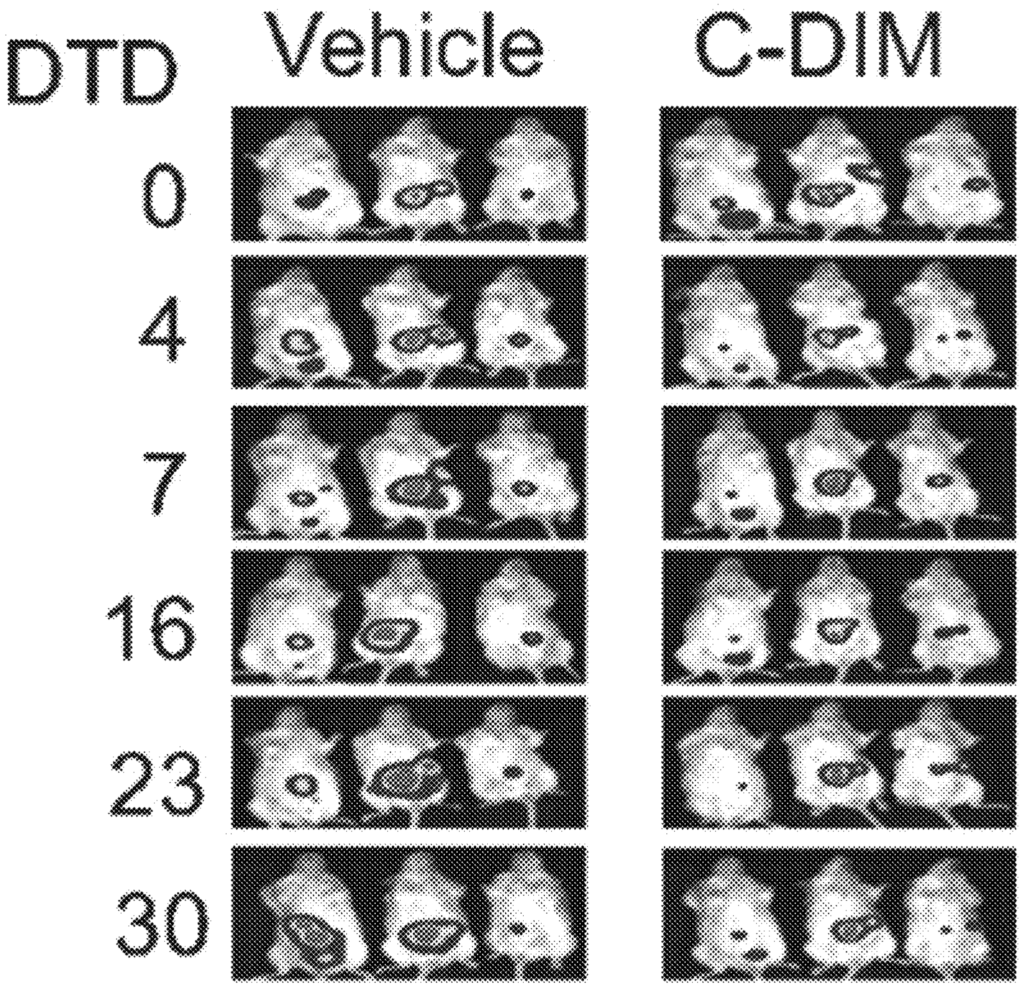
FIG. 9B shows luciferase activities of human ectopic lesions determined at 4, 7, 16, 23, and 30-day after drug treatment, in accordance with an embodiment of the disclosure.
Figure 9C:
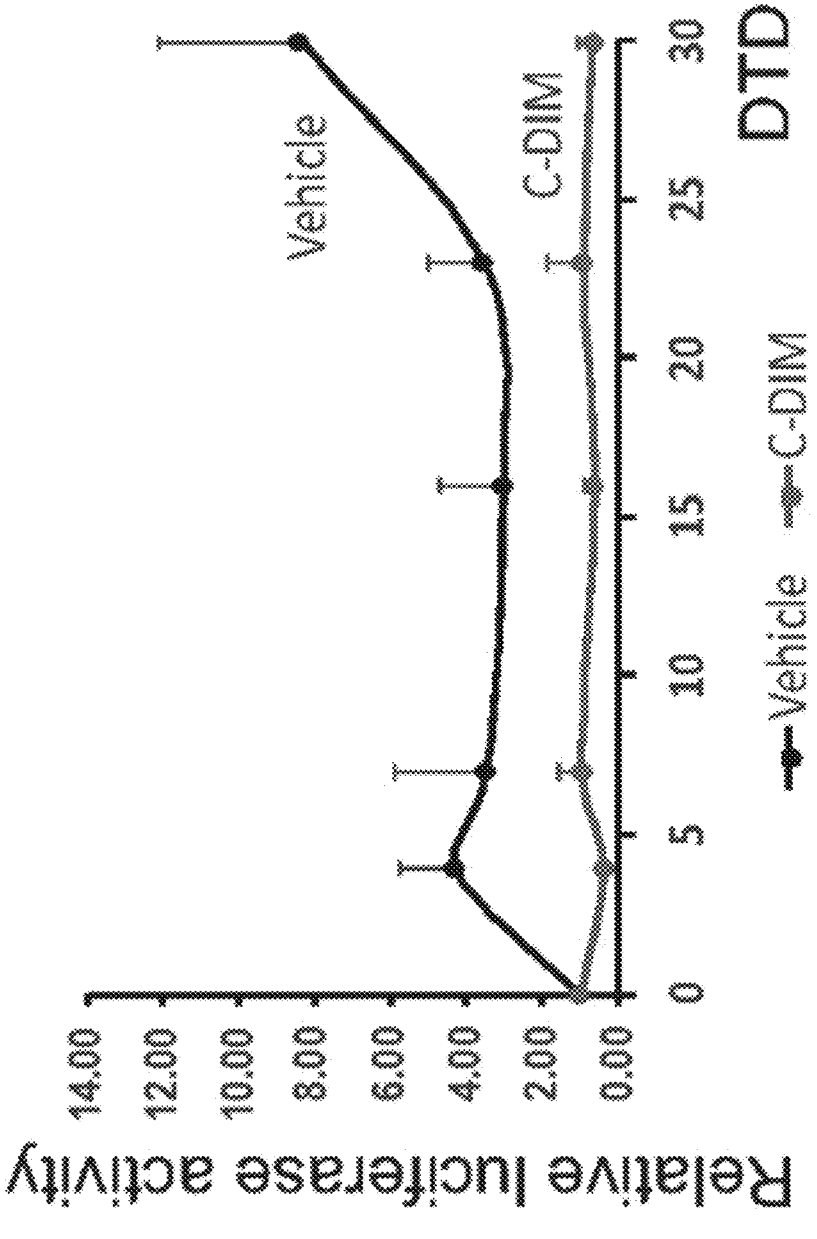
FIG. 9C graphically illustrates the relative fold of luciferase activity compared to 0-day drug treatment, in accordance with an embodiment of the disclosure, based on the luciferase activities shown in FIG. 9B.

The above observation raised the question of whether DIM-C-pPhOH-3-Cl-5-OCH3 also suppresses the growth of human ectopic lesions. To address this question, we induced endometriosis into SCID mice with HECs carrying the luciferase gene. Mice with human ectopic lesions were treated with 25 mg/kg of DIM-C-pPhOH-3-Cl-5-OCH3 versus the vehicle as to the control (FIG. 9A). In addition to mouse ectopic lesions, the DIM-C-pPhOH-3-Cl-5-OCH3 treatment also significantly reduced the luciferase activity in ectopic lesions as compared with the vehicle image (13.4-fold, p=0.022) (FIGS. 9B and 9C). Since the luciferase activity recapitulates the growth of human ectopic lesions in mice, DIM-C-pPhOH-3-Cl-5-OCH3 treatment with the NR4A1 antagonist suppressed the growth of human ectopic lesions in SCID mice compared to the vehicle and demonstrated the in vivo efficacy of NR4A1 antagonists as inhibitors of endometriosis.

ABBREVIATIONS

C-DIM, Methylene substituted diindolylmethane;
COLIA1, collagen type α1;
CTGP, connective tissue growth factor;
DAB, diaminobenzidine;
DIM, 3,3'-diindolylmethane;
DIM-C-pPhOH, 1,1-bis(3'-indolyl)-1-(4-hydroxyphenyl) methane;
EGFR, epidermal growth factor receptor;
FN, fibronectin; HEC, human endometrial cells;
IHC, immunohistochemistry;
NBRE, nerve growth factor β response element;
NR4A, nuclear receptor 4A;
LIHESCs, luciferase stable immortalized human endometrial cells;
PBS, phosphate buffered saline;
PVDF, polyvinylidene fluoride;
SMA, smooth muscle actin.

It will be understood that any embodiment, characteristic, element, definition, or general description provided for any aspect of the disclosure can be applied to any other aspect of the disclosure without limitation, unless explicitly stated. Thus, any embodiment discussed herein can be implemented with respect to any method, agent, or composition of the invention, and vice versa. Furthermore, agents and compositions of the invention can be used to achieve methods of the invention.

The use of the word "a" or "an," when used in conjunction with the term "comprising" herein can mean "one," but it is also consistent with the meaning of "one or more," "at least one," and "one or more than one."

The use of the term "or" is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. As an alternative to or in addition to "comprising," any embodiment herein can recite "consisting of." The transitional phrase "consisting of" excludes any element, step, or ingredient not specified in the claim. Words using the singular or plural number also include the plural and singular number, respectively. Additionally, the words "herein," "above," and "below," and words of similar import, when used in this application, shall refer to this application as a whole and not to any particular portions of the application.

Publications cited herein and the subject matter for which they are cited are hereby specifically incorporated by reference in their entireties.

While the preferred embodiment of the invention has been illustrated and described, it will be appreciated that various changes can be made therein without departing from the spirit and scope of the invention.

The invention claimed is:

1. A method of treating endometriosis in an individual by antagonization of Nuclear Receptor Subfamily 4 Group A Member 1 (NR4A1) activity, the method comprising administering to the individual a therapeutically effective amount of a compound of the formula:

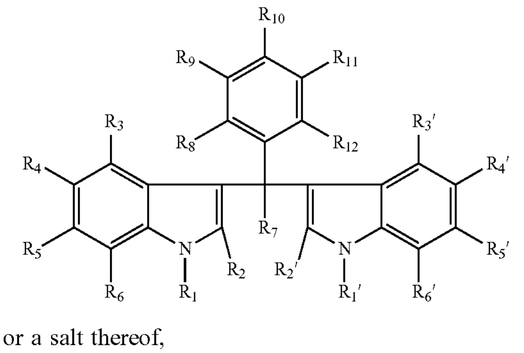

or a salt thereof, wherein, $R_1$, $R_2$, $R_1'$, and $R_2'$ are each independently selected from the group consisting of hydrogen, a linear alkyl group containing one to about ten carbon atoms, and a branched alkyl group containing one to about ten carbon atoms;

$R_3$, $R_4$, $R_5$, $R_6$, $R_3'$, $R_4'$, $R_5'$, and $R_6'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

$R_7$ is selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

$R_8$, $R_9$, $R_{10}$, $R_{11}$, and $R_{12}$ are independently selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a hydroxyl group, and a haloalkoxy group containing one to about ten carbon atoms;

wherein at least one of $R_8$, $R_9$, $R_{10}$, $R_{11}$, and $R_{12}$ is OH, and wherein when $R_{10}$ is OH at least one of $R_8$, $R_9$, $R_{11}$, and $R_{12}$ is not hydrogen.

2. The method of claim 1, wherein $R_8$ is OH.

3. The method of claim 2, wherein $R_9$, $R_{10}$, $R_{11}$, and $R_{12}$ are each H.

4. The method of claim 2, wherein $R_9$, $R_{10}$, $R_{11}$, and $R_{12}$ are independently selected from the group consisting of a halogen, $CH_3$, $OCCl_3$, $CF_3$, t-butyl, $OCH_3$, OH, and $C_6H_5$.

5. The method of claim 2, wherein $R_{10}$ is $OCH_3$.

6. The method of claim 2, wherein R11 is selected from the group consisting of $CH_3$, $OCH_3$, and $CF_3$.

7. The method of claim 2, wherein $R_9$ and $R_{11}$ are Br.

8. The method of claim 2, wherein the compound is selected from the group consisting of:

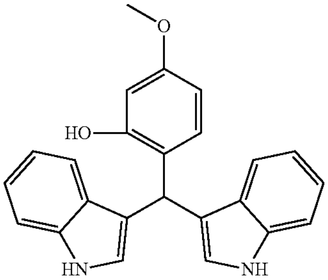
;

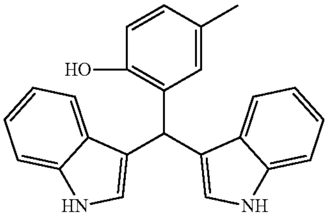
;

-continued

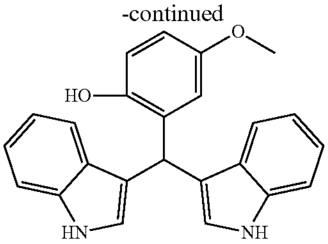
;

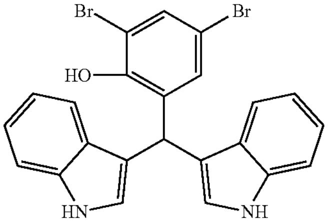
;

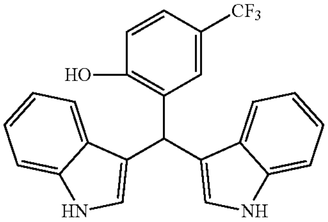
;

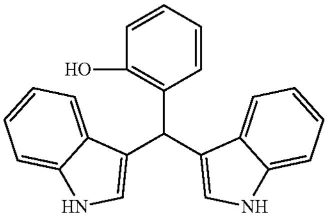
;

and salts thereof.

9. The method of claim 1, wherein $R_9$ is OH.

10. The method of claim 9, wherein $R_8$, $R_{10}$, $R_{11}$, and $R_{12}$ are each H.

11. The method of claim 9, wherein $R_8$, $R_{10}$, $R_{11}$, and $R_{12}$ are independently selected from the group consisting of a halogen, $CH_3$, $OCCl_3$, $CF_3$, t-butyl, $OCH_3$, OH, and $C_6H_5$.

12. The method of claim 9, wherein $R_8$ is a halogen.

13. The method of claim 9, wherein the compound is selected from the group consisting of:

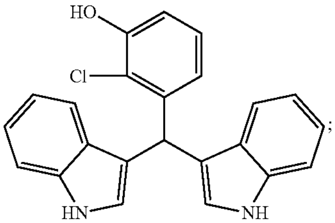
;

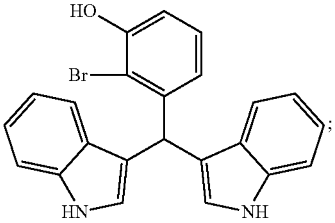
;

-continued

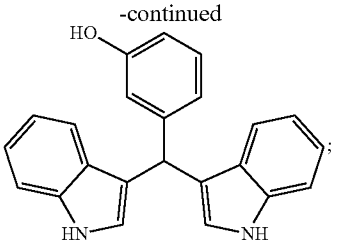

and salts thereof.

14. The method of claim 1, wherein $R_{10}$ is OH.

15. The method of claim 14, wherein $R_8$, $R_9$, $R_{11}$, and $R_{12}$ are independently selected the group consisting of a halogen, $CH_3$, $OCCl_3$, $CF_3$, t-butyl, $OCH_3$, OH, and $C_6H_5$.

16. The method of claim 14, wherein $R_9$ is a halogen and $R_{11}$ is selected from the group consisting of H, a halogen, and $OCH_3$.

17. The compound of claim 14, wherein the compound is selected from the group consisting of:

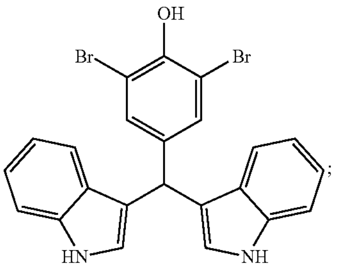

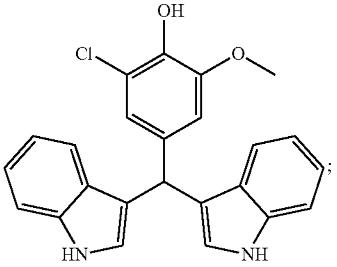

-continued

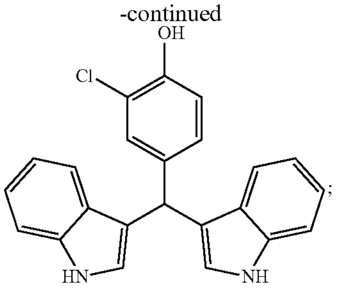

and salts thereof.

18. The method of claim 1, wherein antagonization of NR4A1 induces down-regulation of a protein selected from the group consisting of EFGR, cMyc, survivin, Bcl-2, SMA, and combinations thereof.

19. The method of claim 1, wherein antagonization of NR4A1 activity induces up-regulation of Bax.

20. The method of claim 1, wherein antagonization of NR4A1 activity induces decreased levels of mRNA of fibrosis markers selected from the group consisting of FN, Col1A1, CTGF, and combinations thereof.

21. The method of claim 1, wherein antagonization of NR4A1 activity cleaves PARP and caspase-3.

22. The method of claim 1, wherein antagonization of NR4A1 activity induces apoptosis in ovarian endometrioma.

23. The method of claim 22, wherein antagonization of NR4A1 activity does not inhibit growth of normal endometrial cells relative to a control.

24. The method of claim 1, wherein antagonization of NR4A1 activity inhibits progression of fibrosis.

25. The method of claim 1, wherein antagonization of NR4A1 activity suppresses intrinsic transcriptional activity of NR4A1 in endometriotic cells relative to a control.

26. The method of claim 1, wherein antagonization of NR4A1 activity suppresses growth of ectopic lesions relative to a control.

* * * * *